United States Patent
Altman

(10) Patent No.: US 11,241,464 B2
(45) Date of Patent: Feb. 8, 2022

(54) METHODS OF IMPROVING REPRODUCTIVE AND RESPIRATORY HEALTH

(71) Applicant: ALTERA INTERNATIONAL, LTD., Fort Collins, CO (US)

(72) Inventor: Jay A. Altman, Fort Collins, CO (US)

(73) Assignee: Altera International, LTD., Fort Collins, CO (US)

(*) Notice: Subject to any disclaimer, the term of this patent is extended or adjusted under 35 U.S.C. 154(b) by 13 days.

(21) Appl. No.: 14/897,794

(22) PCT Filed: Jun. 13, 2014

(86) PCT No.: PCT/US2014/042354
§ 371 (c)(1),
(2) Date: Dec. 11, 2015

(87) PCT Pub. No.: WO2014/201387
PCT Pub. Date: Dec. 18, 2014

(65) Prior Publication Data
US 2016/0106790 A1    Apr. 21, 2016

Related U.S. Application Data

(60) Provisional application No. 61/834,656, filed on Jun. 13, 2013.

(51) Int. Cl.
*A61K 36/02*    (2006.01)
*A61K 31/202*   (2006.01)
(Continued)

(52) U.S. Cl.
CPC ............ *A61K 36/02* (2013.01); *A61K 31/095* (2013.01); *A61K 31/202* (2013.01);
(Continued)

(58) Field of Classification Search
CPC .. A61K 2300/00; A61K 31/202; A61K 31/10; A61K 31/60; A61K 31/519; A61K 33/26; A61K 33/30; A61K 45/06; A61K 31/12; A61K 31/47; A61K 33/06; A61K 36/07; A61K 36/074; A61K 31/17; A61K 31/201; A61K 31/7004; A61K 33/14; A61K 36/06; A61K 36/068; A61K 36/076; A61K 36/67; A61K 9/1688; A61K 31/07; A61K 31/20; A61K 31/355; A61K 31/375; A61K 31/4415; A61K 31/455; A61K 31/51; A61K 31/525; A61K 31/59; A61K 31/714; A61K 33/18; A61K 33/34; A61K 36/185; A61K 36/30; A61K 36/48; A61K 31/085; A61K 31/14; A61K 31/198; A61K 36/00; A61K 36/16; A61K 36/31; A61K 8/46; A61K 9/4858; A61K 9/4866; A61K 31/4045; A61K 31/45255; A23V 2002/00; A23V 2200/08; A23V 2250/0612; A23V 2250/0616; A23V 2250/063; A23V 2250/15; A23V 2250/186; A23V 2250/21; A23V 2250/708; A23V 2250/712; A23L 33/16; A23L 33/15; A23L 1/304; A23L 33/115; A23L 33/12; A23L 1/3006; A23L 1/3008; A23L 1/302; A23L 27/2022; A23L 29/055; A23L 33/10; A23L 33/105; A23L 33/17; A23L 1/0029; A23L 1/296; A23L 1/3002; A23L 1/305; A23L 1/3051; A23L 21/00; A23L 2/52; A23L 31/00; A23L 33/125; A23L 33/155; A23L 33/175; A23L 5/00; A23L 7/00; A61P 3/02; A61P 29/00; A61P 31/00; A61P 43/00; A61P 1/00; A61P 31/18; A61P 3/00; A61P 11/00; A61P 11/02; A61P 11/14; A61P 15/00; A61P 17/00; A61P 17/06; A61P 19/00; A61P 19/02; A61P 1/12; A61P 1/14; A61P 1/16; A61P 25/28; A61P 31/12; A61P 33/00; A61P 35/00; A61P 35/02; A61P 35/04; A61P 37/04; A61P 37/08; A61P 3/10; A61P 9/12; A23K 10/30; A23K 20/158; A23K 50/20; A23K 20/10; A23K 20/105; A23K 20/111; A23K 20/142; A23K 20/174; A23K 20/179; A23K 20/20; A23K 20/24; A23K 20/30; A23K 1/1603; A23K 1/1606;
(Continued)

(56) References Cited

U.S. PATENT DOCUMENTS 4,559,329 A * 12/1985 Herschler ............ A61K 9/1688
                                                        514/164
4,616,039 A   10/1986 Herschler
(Continued)

FOREIGN PATENT DOCUMENTS

WO   WO2004/032918 A1 *  4/2004  ............ A61K 31/20
WO   WO2007/126221    * 11/2007  ............ A61K 36/748
WO      2014201387 A2   12/2014

OTHER PUBLICATIONS

Downer et al. ("Effects of an Oral Nutraceutical on Clinical Aspects of Joint Disease in a Blinded, Controlled Trial: 39 Horses", Surgery—Lameness, AAEP Proceedings, 2007, vol. 53, p. 252-255).*
(Continued)

*Primary Examiner* — Audrea B Coniglio
(74) *Attorney, Agent, or Firm* — Polsinelli PC

(57) ABSTRACT

The present invention encompasses methods of improving reproductive and respiratory health.

5 Claims, 11 Drawing Sheets

(51) Int. Cl.
*A61K 31/355* (2006.01)
*A61K 31/593* (2006.01)
*A61K 36/06* (2006.01)
*A61K 36/55* (2006.01)
*A61K 31/375* (2006.01)
*A61K 31/095* (2006.01)
*A61K 45/06* (2006.01)

(52) U.S. Cl.
CPC .......... *A61K 31/355* (2013.01); *A61K 31/375* (2013.01); *A61K 31/593* (2013.01); *A61K 36/06* (2013.01); *A61K 36/55* (2013.01); *A61K 45/06* (2013.01)

(58) Field of Classification Search
CPC .. A23K 1/1612; A23K 1/1631; A23K 1/1634; A23K 1/164; A23K 1/1646; A23K 1/175; A23K 1/1753; A23K 1/1758; A23K 1/1806; A23K 20/147; A23K 20/168; A23K 50/40
See application file for complete search history.

(56) References Cited

U.S. PATENT DOCUMENTS

| | | | |
|---|---|---|---|
| 6,403,631 | B1 | 6/2002 | Sharp et al. |
| 8,545,896 | B2 * | 10/2013 | Perrin ................... A61K 31/07 424/638 |
| 2003/0157190 | A1 | 8/2003 | Woods et al. |
| 2005/0037065 | A1 | 2/2005 | Kirschner et al. |
| 2006/0171958 | A1 * | 8/2006 | Stamets ................ A61K 36/07 424/195.15 |
| 2007/0259367 | A1 | 11/2007 | Ax et al. |
| 2009/0149539 | A1 | 6/2009 | Kelley et al. |
| 2009/0304827 | A1 * | 12/2009 | Kim ....................... A61K 31/12 424/725 |
| 2011/0021461 | A1 | 1/2011 | Vazquez-Anon et al. |
| 2011/0206721 | A1 * | 8/2011 | Nair ....................... A61K 36/06 424/195.15 |
| 2012/0058087 | A1 | 3/2012 | Petersen et al. |
| 2012/0197067 | A1 | 8/2012 | Kat et al. |

OTHER PUBLICATIONS

Lowell ("Observations on heaves. An asthma-like syndrome in the horse", Francis C. Lowell M.D., Journal of Allergy, vol. 35, Issue 4, Jul.-Aug. 1964, pp. 322-330) (Year: 1964).*

International Search Report and Written Opinion dated Dec. 13, 2015 from related International Patent Application No. PCT/US2014/042354/012200; 5 pgs.

Office action dated Feb. 19, 2020 from related Canadian Application No. 2,913,776, 4 pgs.

Schell, "Medicinal Mushrooms and Your Horse", The Northwest Horse Source, https://www.nwhorsesource.com/medicinal-mushrooms-and-your-horse/, May 1, 2013, 11 pages.

* cited by examiner

METHODS OF IMPROVING REPRODUCTIVE AND RESPIRATORY HEALTH

CROSS REFERENCE TO RELATED APPLICATIONS

This application claims the benefit of PCT International Application No. PCT/US2014/042354, filed Jun. 13, 2014, which claims the priority of U.S. provisional application No. 61/834,656, filed Jun. 13, 2013, each of the disclosures of which are hereby incorporated by reference in its entirety.

FIELD OF THE INVENTION

The present invention is directed to methods of improving reproductive and respiratory health.

BACKGROUND OF THE INVENTION

Reproductive Health

Persistent mating induced endometritis is a multifactorial condition resulting in delayed uterine clearance, persistent inflammation and reduced fertility. In the mare, the acute inflammation that follows breeding is a normal physiologic response and necessary to facilitate clearance of contaminants, excessive sperm and seminal plasma from the uterus. Uterine inflammation should be completely resolved by 48 h of breeding (LeBlanc M M, 2009). Persistent mating induced endometritis is judged by practitioners to be the most common cause of infertility and has been shown to occur in 15% of normal Thoroughbred mares (Zent W, 1998).

There is a need in the art for methods of decreasing persistent mating induced endometritis.

Offspring Health

Maternal docosahexaenoic acid (DHA) has been linked to positive developmental outcomes in infants. For example, exposure to maternal DHA during gestation and lactation contributes toward improved mental development, childhood learning, and behavioral reactivity in humans. In foals, the influence of maternal DHA intake on their behavior and cognitive development has not been examined. Since positive behavior and cognitive development are important in the developing foal, there is a need for the supplementation of mares during late gestation and early lactation to positively influence foal behavior and learning ability.

Respiratory Health

Chronic lower airway inflammatory diseases commonly occur in horses. Recurrent airway obstruction (RAO), also known as heaves, is more prevalent in stabled horses in wet, cool climates in mature to older animals, while inflammatory airway disease (IAD) can occur under any environmental condition and can affect horses of any age, but tends to be more common in the younger population (Couetil et al. 2007).

Horses affected with chronic lower airway inflammatory diseases need long term (IAD) or even lifelong (RAO) management that can require significant financial and time commitments from owners. Ideal strict environmental management achieves maintenance of clinical remission in the majority of horses. Hence, there is a need in the art for methods of ameliorating chronic lower airway inflammatory disease.

SUMMARY OF THE INVENTION

In an aspect, the invention encompasses a method for improving the per cycle pregnancy rate for maiden or barren equine mares. The method comprises administering a composition comprising Composition A at a daily dose of between 4-7 g per 110 lbs of body weight at least 10 days before coitus, and continuing to dose daily till at least 2 days post-coitus.

In another aspect, the invention encompasses a method for reducing chronic respiratory disease in an equid. The method comprises administering 2-4 g of Composition B per 110 lbs body weight for at least two weeks.

In still another aspect, the invention encompasses a method for increasing DHA availability to foals. The method comprises administering to a pregnant mare a composition comprising Composition A at a daily dose of between 4-7 g per 110 lbs of body weight at least 30 days before expected foaling, and continuing to dose daily through at least 30 days lactation.

In still yet another aspect, the invention encompasses a method for improving behavior and cognitive development in nursing foals. The method comprises administering to a pregnant mare a composition comprising Composition A at a daily dose of between 4-7 g per 110 lbs of body weight at least 30 days before expected foaling, and continuing to dose daily through at least 30 days lactation.

In yet still another aspect, the invention encompasses a method for improving reproductive function in postpartum mares. The method comprises administering to a pregnant mare a composition comprising Composition A at a daily dose of between 4-7 g per 110 lbs of body weight at least 30 days before expected foaling, and continuing to dose daily through at least one postpartum ovulation.

In yet still another aspect, the invention encompasses a method for reducing the post-breeding inflammatory response. The method comprises administering to a mare a composition comprising Composition A at a daily dose of between 4-7 g per 110 lbs of body weight at least 10 days before coitus, and continuing to dose daily till at least 2 days post-coitus.

DETAILED DESCRIPTION

Figure 1:
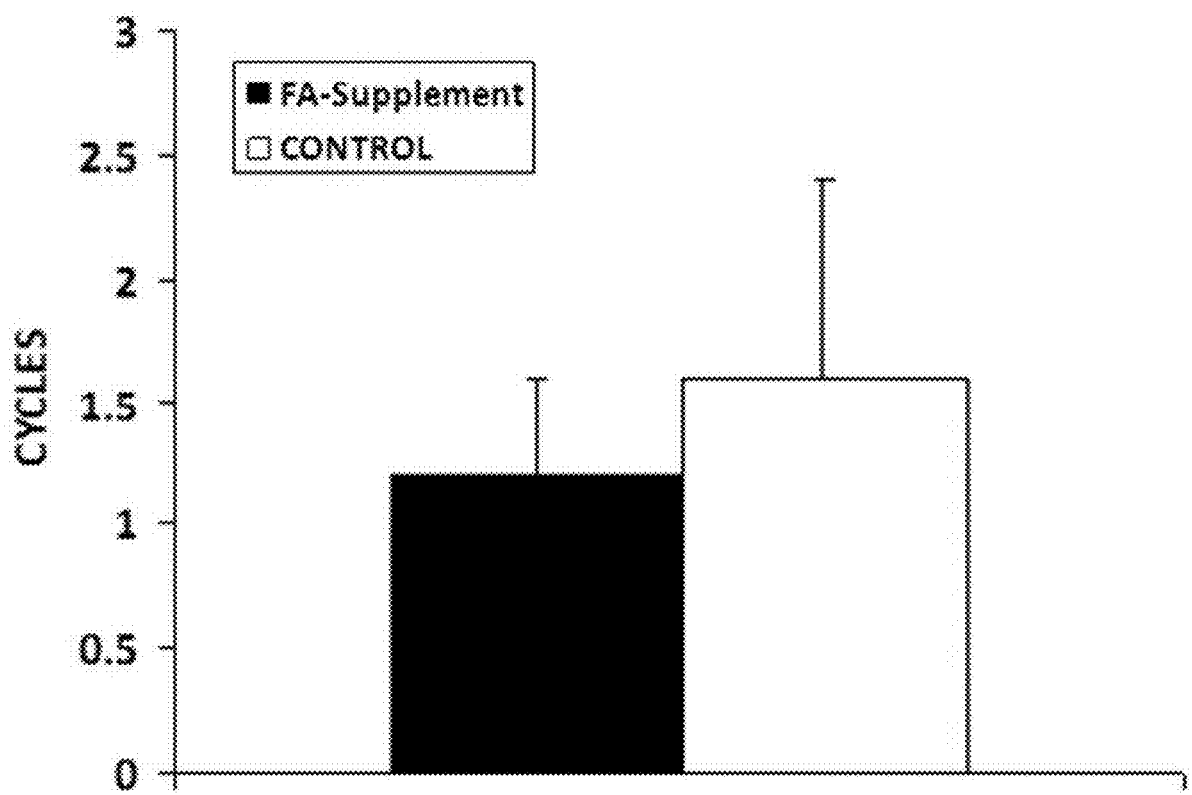
FIG. 1: Per cycle pregnancy rates of Thoroughbred mares bred by natural service supplemented with an N-3 Fatty acid supplement, FA-SUPPLEMENT (1.19±0.40) or No Supplement (CONTROL; 1.59±0.81). The FA-SUPPLEMENT supplemented ration contained 14,400 mg of combined n-3 fatty acids of which 4,000 mg were DHA (P=0.026).

The present invention provides methods and compositions for improving reproductive and respiratory health.

I. Reproductive Health

One aspect of the present invention encompasses a method for improving the reproductive health of a subject. In some embodiments, a method of the invention reduces post-coital uterine inflammation. In other embodiments, a method of the invention improves the per cycle pregnancy rate of the subject. In still other embodiments, a method of the invention reduces uterine fluid 24 hours post-coitus. In still yet other embodiments, a method of the invention improves reproductive function in a postpartum subject. Reproductive function in a postpartum subject may be improved by hastening uterine involution and/or increasing ovarian blood flow.

As used within Section I, subject refers to a female mammal. In some embodiments, the female is "maiden," meaning that the female has not yet carried a pregnancy to term. In other embodiments, the female is "barren," meaning that the female has failed to conceive, despite accurately timed coitus, for at least six cycles (menstrual or estrus cycles), or a female that has lost a pregnancy due to early embryonic loss or spontaneous abortion. In still other embodiments, the female is "postpartum," meaning that the female has given birth. Generally speaking, the postpartum period is the period beginning immediately after the birth and extending for about 6 months.

In certain embodiments, the female is human. In these embodiments, a "maiden" refers to a human female that has not yet carried a pregnancy to term, a "barren" female refers to a human female that has not conceived for six menstrual cycles, or six IVF cycles, or a female that has lost a pregnancy in the last 12 months due to early embryonic loss or spontaneous abortion, and a "postpartum" female refers to a human female that has given birth to a child within about 6 months prior.

In other embodiments, the female is a livestock animal. Suitable livestock animals may include equids, sheep, goats, llamas, alpacas, and bovines. In an exemplary embodiment, the female is equine. In this context, a "maiden" refers to an equine mare that has not yet carried a pregnancy to term. A "barren" mare refers to a mare that failed to conceive or carry to term in the previous breeding season, or that has lost a pregnancy due to early embryonic loss or spontaneous abortion in the present breeding season. A "postpartum" mare refers to a mare that has given birth to a foal within about 6 months prior.

Generally speaking, a method of the invention encompasses administering a composition (hereinafter referred to as Composition A) to a subject before coitus. In an embodiment, composition A may be administered to a pregnant subject prior to expected birth and continuing through postpartum ovulation. Composition A is described in more detail below. Generally, the method comprises administering, orally, 4-7 grams of Composition A per 110 lb of subject body weight daily. For equines, for instance, 60-120 grams per mare per day may be administered. Generally speaking, administration is daily, and should start at least 1, 2, 3, 4, 5, 6, 7, 8, 9, 10, 15, 20, 25, 30, 35, 40, 45, 50, 55 or 60 days prior to coitus, and then continue post-coitus. Post-coitus administration may occur for at least 1, 2, 3, 4, 5, 6, 7, 8, 9, 10 or 15 days. In an embodiment, daily administration should start at least 1, 2, 3, 4, 5, 6, 7, 8, 9, 10, 15, 20, 25, 30, 35, 40, 45, 50, 55, 60, 70, 80, or 90 days prior to expected birth, and then continue through postpartum ovulation. Administration may continue through 1, 2, 3, 4, 5 or 6 cycles of postpartum ovulation.

In some embodiments, a higher dose is administered initially, followed by a maintenance dose. The higher dose may be between 1.5 to 2.5 times the maintenance dose. By way of non-limiting example, an equine mare may be administered the high dose (120 grams per day) for 30 days before coitus and through 90 days post-coitus (e.g. into gestation) and then a maintenance dose of 60 gram per day may be used through the rest of gestation, if desired.

(a) Composition A

Composition A of the invention comprises DHA (docosahexaenoic acid). In some embodiments, the DHA is algal DHA. In exemplary embodiments, the DHA is from an all-vegetarian, fish oil-free source. A dose of Composition A generally comprises at least 1500, 1600, 1700, 1800, 1900, 2000, 2100, or 2200 mg of DHA per 60 g of composition. Stated another way, Composition A generally comprises between about 20% and about 30% DHA. In some embodiments, Composition A comprises about 20, 21, 22, 23, 24, 25, 26, 27, 28, 29 or 30% DHA.

In certain embodiments, Composition A further comprises a total omega-3 fatty acid amount of at least 5,000, 5,500, 6,000, 6,500, or 7000 mg per 60 g of composition. For instance, Composition A may comprise about 6500, 6600, 6700, 6800, 6900, 7000, 7100, 7200, 7300, 7400, or 7500 mg total omega-3 fatty acid per 60 g of composition. In some embodiments, Composition A may comprise between about 7000 and about 7500 mg total omega-3 fatty acid 60 g of composition. Stated another way, Composition A has between about 45% and 75% total omega-3 fatty acids. In certain embodiments, Composition A has about 50, 51, 52, 53, 54, 55, 56, 57, 58, 59, 60, 61, 62, 63, 64 or 65% total omega-3 fatty acids. In preferred embodiments, the omega-3-fatty acid is from fish-oil-free source, such as flaxseed, or flaxseed meal.

Composition A may also further include ingredients selected from the group consisting of vitamins, antioxidants, roughage, feed grade fat, sweeteners, preservatives, and flavorings. Suitable vitamins may include vitamin E, vitamin D, and vitamin C. For instance, Composition A may comprise about 4000 IU, 4500 IU, 5000 IU, 5500 IU, 6000 IU, 6500 IU, or 7000 IU Vitamin D per 60 grams of total composition. In exemplary embodiments, Composition A may comprise about 4000 IU, 4500 IU, 5000 IU, 5500 IU, 6000 IU, 6500 IU, or 7000 IU Vitamin D3 per 60 grams of total composition. In some embodiments, Composition A may comprise 500, 600, 700, 800, 900, 1000, 1100, 1200, 1300, 1400, or 1500 IU Vitamin E per 60 grams of total composition. Suitable antioxidants may include vitamin C (ascorbic acid). Suitable roughage sources may include alfalfa meal. Composition A may comprise between about 0.05% and 3% roughage. Suitable sweeteners may include sugar, molasses, sugar alcohols, saccharin, or other sweeteners. Suitable artificial flavors are known in the art. Generally speaking, Composition A may comprise between about 1% and 15% artificial flavorings and sweeteners. Suitable preservatives may include organic acids, such as propionic acid. In some embodiments, Composition A may comprise between about 0.01% and 5% preservatives.

In one embodiment, composition A comprises flaxseed meal, algal DHA, vitamin E, vitamin D3, sorbitol, ascorbic acid, alfalfa meal, sodium saccharin, propionic acid and artificial flavor. In an exemplary embodiment, Composition A comprises total omega-3 fatty acids of 7,200 mg, DHA of 2,000 mg, Vitamin D3 of 6000 IU, and Vitamin E of 1000 IU per 60 grams of total composition.

Composition A may also be described in terms of macronutrients. For instance, Composition A generally has between 0.5 and 15% (w/w) protein. In some embodiments, Composition A has between 8 and 12% (w/w) protein. Composition A generally has between 20% and 45% (w/w) fat. In some instances, Composition A has between 28% and 45% (w/w) fat. In other instances, Composition A has between 20% and 35% (w/w) fat. Generally speaking, Composition A has between about 10% and 20% (w/w fiber). In an exemplary embodiment, Composition A has 10% (w/w) protein, 24% (w/w) fat and 15% (w/w) fiber, by weight of the total composition.

In an exemplary embodiment, Composition A comprises about 22%-26% DHA, about 55%-63% flaxseed, about 0.5-2% alfalfa meal, about 3.5-5% sweeteners, and about 0.5-1.5% preservatives.

In an exemplary embodiment, Composition A is RELEIRA®.

(b) Combinations

Composition A of the invention may also be administered simultaneously or in conjunction with other treatments intended to improve or monitor reproductive health. For instance, composition A may be administered in conjunction with post-coital uterine lavage or intra-uterine antibiotics. Or Composition A may be administered with routine breeding farm management, such as testing for negative uterine culture and cytology prior to breeding, daily monitoring when in estrus using rectal palpation and transrectal ultrasound examination associated with breeding. Composition A may be administered in conjunction with ovulation inducing agents such as HCG (Chorulon, Intervet, De Soto, Kans.) or Deslorelin (SucroMate Equine, Thorn BioScience LLC, Louisville, Ky.). In still other embodiments, Composition A may be administered in conjunction with oxytocin to facilitate uterine evacuation.

(c) Preferred Methods

In exemplary embodiments, the invention provides a method of decreasing the per cycle pregnancy rate for an equine mare. As used herein, "per cycle pregnancy rate" refers to the number of cycles required for the female subject to conceive. In a further exemplary embodiment, the invention provides a method of decreasing the per cycle pregnancy rate for a maiden or barren equine mare. Generally speaking, the method comprises daily administration of Composition A starting at least 10, 15, 20, 25, or 30 days before coitus, at a dose of between about 4-7 g per 110 lbs of body weight (40-70 g per 1100 lbs of body weight). Administration should continue post-coitus for at least 10 days, but may extend further if desired. For instance, administration may extend 10, 15, 20, 25, 30, 45, 60, 75, 90, or more than 90 days post-coitus.

In another exemplary embodiment, the invention provides a method of reducing uterine fluid present at 24 hours post-coitus for an equine mare. Generally speaking, the method comprises daily administering composition A starting at least 10, 15, 20, 25, or 30 days before coitus, at a dose of between about 4-7 g per 110 lbs of body weight (40-70 g per 1100 lbs of body weight). Administration should continue post-coitus for at least 10 days, but may extend further if desired. For instance, administration may extend 10, 15, 20, 25, 30, 45, 60, 75, 90, or more than 90 days post-coitus. Methods of monitoring uterine fluid are known in the art, and previous data from the same mare may be used as a comparison.

In still another exemplary embodiment, the invention provides a method of reducing post-coital uterine inflammation for an equine mare. Generally speaking, the method comprises daily administering composition A starting at least 10, 15, 20, 25, 30, 45 or 60 days before coitus, at a dose of between about 4-7 g per 110 lbs of body weight (40-70 g per 1100 lbs of body weight). Administration should continue post-coitus for at least 10 days, but may extend further if desired. For instance, administration may extend 10, 15, 20, 25, 30, 45, 60, 75, 90, or more than 90 days post-coitus. Methods of monitoring post-coital uterine inflammation are known in the art, and previous data from the same mare may be used as a comparison.

In still yet another exemplary embodiment, the invention provides a method for improving reproductive function in a postpartum mare. Generally speaking, the method comprises administering to a pregnant mare a composition comprising Composition A at a daily dose of between 4-7 g per 110 lbs of body weight at least 30, 45, 60, 75, or 90 days before expected foaling. Administration should continue through at least the first postpartum ovulation, but may extend further if desired. For instance, administration may extend through the second, third, fourth, fifth or sixth postpartum ovulation. The method of improving reproductive function hastens uterine involution and increases ovarian blood flow. Methods of monitoring reproductive function are known in the art, and previous data from the same mare may be used as a comparison.

II. Offspring Health

Another aspect of the present invention encompasses a method for improving the health of an offspring of a subject. In some embodiments, a method of the invention increases DHA availability to offspring. The DHA availability to offspring may be increased by increased DHA in umbilical cord plasma and increased DHA in milk produced by the subject. In other embodiments, a method of the invention improves behavior and cognitive development in nursing offspring. The behavior and cognitive development may be increased by increased engagement in social affiliative, increased nursing, and/or increased lying down.

As used within Section II, subject refers to a female mammal. In certain embodiments, the female is human. In other embodiments, the female is a livestock animal. Suitable livestock animals may include equids, sheep, goats, llamas, alpacas, and bovines. In an exemplary embodiment, the female is equine. An offspring is a product of reproduction produced, in part, by the subject. Suitable offspring may include the offspring of a female mammal. In certain embodiments, the offspring is a child. In an exemplary embodiment, the offspring is a foal.

Generally speaking, a method of the invention encompasses administering Composition A as described in Section I(a) to a subject during pregnancy. In an embodiment, composition A may be administered to a subject following birth of the offspring through lactation. Generally, the method comprises administering, orally, 4-7 grams of Composition A per 110 lb of subject body weight daily. For equines, for instance, 60-120 grams per mare per day may be administered. Generally speaking, administration should start at least 1, 2, 3, 4, 5, 6, 7, 8, 9, 10, 15, 20, 25, 30, 35, 40, 45, 50, 55, 60, 70, 80, or 90 days prior to expected birth, and then continue through lactation. Administration may continue through at least 1, 2, 3, 4, 5, 6, 7, 8, 9, 10, 15, 20, 25, 30, 35, 40, 45, 50, 55, 60, 70, 80, or 90 days of lactation.

(a) Preferred Methods

In exemplary embodiments, the invention provides a method for increasing DHA availability to foals. An increase in DHA availability may be measured through an increase in DHA in plasma, red blood cells, umbilical cord plasma, and milk in mares or an increase in DHA in plasma in foals. Generally speaking, the method comprises daily administration of Composition A starting at least 30, 40, 50, 60, 70, 80 or 90 days before expected foaling, at a dose of between about 4-7 g per 110 lbs of body weight (40-70 g per 1100 lbs of body weight). Administration should continue through lactation for at least 30 days, but may extend further if desired. For instance, administration may extend 30, 40, 50, 60, 70, 80 or 90 days, or more than 90 days through lactation.

In another exemplary embodiment, the invention provides a method for improving behavior and cognitive development in nursing foals. An improvement in behavior and cognitive development may be measured by an increase in engagement in social affiliative, an increase in nursing and/or an increase in lying down. Generally speaking, the method comprises daily administration of Composition A starting at least 30, 40, 50, 60, 70, 80 or 90 days before expected foaling, at a dose of between about 4-7 g per 110 lbs of body weight (40-70 g per 1100 lbs of body weight). Administration should continue through lactation for at least 30 days, but may extend further if desired. For instance, administration may extend 30, 40, 50, 60, 70, 80 or 90 days, or more than 90 days through lactation.

III. Respiratory Health

Another aspect of the present invention encompasses a method for improving the respiratory function of subjects afflicted with chronic respiratory disease. As used herein, "chronic" refers to an at least 4-week duration coupled with the exhibition of clinical signs of lower airway inflammation, such as coughing, excessive mucous production in the trachea and/or increased respiratory effort at rest and exercise intolerance/poor performance.

As used within Section III, subject refers to a mammal afflicted with chronic respiratory disease. In one embodiment, the subject is human. In other embodiments, the subject may be a livestock animal. Suitable livestock animals may include equids, sheep, goats, llamas, alpacas, and bovines.

Generally speaking, a method of the invention encompasses administering a composition (hereinafter referred to as Composition B) to a subject afflicted with chronic respiratory disease. Composition B is described in more detail below. Generally, feed 2-4 grams of Composition B per 110 lb of subject body weight daily. For equids, for instance, use 20-40 grams per 1100 lb of body weight per day. Generally speaking, Composition B should be administered daily for at least 2 weeks. In some embodiments, Composition B should be administered daily for 2, 3, 4, 5, 6, 7, 8 or more than 8 weeks.

(a) Composition B

Composition B of the invention comprises DHA. In some embodiments, the DHA is algal DHA. In exemplary embodiments, the DHA is from an all-vegetarian, fish oil-free source. A dose of composition B generally comprises at least 700, 800, 900, 1000, 1100, 1200, 1300, 1400, 1500, 1600, 1700, 1800, 1900, or 2000 mg of DHA per 30 g of composition. Stated another way, Composition B comprises about 30% to about 50% DHA. In some embodiments, Composition B comprises about 35, 36, 37, 38, 39, 40, 41, 42, 43, 44, or 45% DHA.

In exemplary embodiments, Composition B further comprises at least one mushroom. By way of non-limiting example, the at least one mushroom may be from the following species: *Agaricus blazei* (Himematsutake), *Antrodia comphorata*, *Coriolus versicolor* (Turkey Tail), *Grifola frondosa* (Maitake), *Hericium erinaceus* (Lion's Mane), *Hypsizygus marmoreus* (Beech), *Cordyceps militaris*, *Ganoderma lucidum* (Reishi) and *Pleurotus eryngii* (King Trumpet). Composition B may comprise one, two, three, or more than three mushrooms. For instance, in an exemplary embodiment Composition B comprises King Trumpet (*Pleurotus eryngii*) mushrooms, Cordyceps (*Cordyceps militaris*) mushrooms, and Reishi (*Ganoderma lucidum*) mushrooms. In another exemplary embodiment, Composition B comprises the ARM2-4 Mushroom Powder Blend from Mycelial Science. In each of the above embodiments, Composition B may comprise at least about 1000, 1250, 1500, 1750, 2000, 2250, 2500, 2750, or 3000 mg mushroom per 30 g dose. In certain embodiments, Composition B may comprise at least about 1500, 1600, 1700, 1800, 1900, 2000, 2100, 2200, 2300, 2400, or 2500 mg mushroom per 30 g dose. In one exemplary embodiment, Composition B comprises about 2000 mg per 30 g dose of a combination of King Trumpet (*Pleurotus eryngii*) mushrooms, Cordyceps (*Cordyceps militaris*) mushrooms, and Reishi (*Ganoderma lucidum*) mushrooms. Stated another way, Composition B may comprise about 5% to about 12% mushrooms. In some embodiments, Composition B may comprise about 5, 6, 7, 8, 9, 10, 11, or 12% mushrooms. In an exemplary embodiment, Composition B may comprise about 5, 6, 7, 8, 9, 10, 11, or 12% of a mixture of King Trumpet (*Pleurotus eryngii*) mushrooms, Cordyceps (*Cordyceps militaris*) mushrooms, and Reishi (*Ganoderma lucidum*) mushrooms.

In certain embodiments, composition B further comprises methylsulfonylmethane (MSM) in an amount of at least 3500, 4000, 4500, 5000, 5500, or 6000 mg per 30 g of composition. For instance, composition B may comprise about 4500, 4600, 4700, 4800, 4900, 5000, 5100, 5200, 5300, 5400, or 5500 mg methylsulfonylmethane per 30 g of composition. In some embodiments, composition B may comprise between about 4800 and about 5200 mg methylsulfonylmethane per 30 g of Composition B. Stated another way, Composition B may comprise between about 10% and 30% MSM. In some embodiments, Composition B may comprise about 15, 16, 17, 18, 19, 20, 21, 22, 23, 24, or 25% MSM.

Composition B may also further include ingredients selected from the group consisting of vitamins, antioxidants, roughage, feed grade fat, sweeteners, preservatives, and flavorings. Suitable vitamins may include vitamin E, vitamin D, and vitamin C (ascorbic acid). For instance, Composition B may include at least 500, 600, 700, 800, 900, 1000, 1100, 1200, 1300, 1400, or 1500 mg ascorbic acid per 30 g. Suitable roughage sources may include alfalfa meal. In some embodiments, Composition B may comprise about 5% to about 15% roughage. For instance, Composition B may comprise about 8, 9, 10, 11, or 12% roughage. Suitable sweeteners may include sugar, molasses, sugar alcohols, saccharin, or other sweeteners. Suitable preservatives may include organic acids, such as propionic acid. Suitable artificial flavors are known in the art.

In one embodiment, Composition B comprises a mushroom blend, DHA, mixed tocopherols, ascorbic acid, propionic acid, alfalfa meal, artificial flavor and sweeteners. In one embodiment, composition B may comprise 5,000 mg methylsulfonylmethane, 2,000 mg mushroom blend, 1,500 mg DHA and 1,000 mg ascorbic acid per 30 g dose. The DHA is from an all-vegetarian, fish oil-free source.

In certain embodiments, Composition B comprises between about 30% and about 50% DHA, about 5% to about 12% mushrooms, about 4% to about 12% mixed tocopherols, about 5% to about 15% alfalfa meal, about 15% to about 25% msm, about 2% to about 8% sweeteners and artificial flavorings, and about 0.05% to about 0.5% preservatives.

In an exemplary embodiment, Composition B is ALEIRA®.

(b) Combinations

Composition B of the invention may also be administered simultaneously or in conjunction with other treatments intended to improve or monitor respiratory health. For instance, in one embodiment, Composition B is fed in conjunction with a low dust diet. In certain circumstances, this may encompass feeding a hay free diet.

(c) Preferred Embodiments

In one embodiment where the subject is an equid, the chronic respiratory disease is chronic recurrent airway obstruction (RAO). In another embodiment where the subject is an equid, the chronic respiratory disease is chronic inflammatory airway disease (IAD). In either embodiment, a method of the invention encompasses administering daily 2-4 g of Composition B per 110 lbs body weight to reduce or alleviate the chronic respiratory disease.

In another preferred embodiment, a method of the invention encompasses reducing the neutrophils present in the lung mucus of a subject with chronic respiratory disease. The neutrophils are reduced compared to the subject before administration of Composition B. The method comprises administering daily 2-4 g of Composition B per 110 lbs body weight of the subject.

EXAMPLES

The following non-limiting examples are included to illustrate the invention.

Example 1

Omega-3 Fatty Acids and Equine Post-Breeding Inflammation—Materials and Methods

Forty-six (Maiden, N=6; Barren, N=40) open thoroughbred mares, ages 4-23 years were used in the testing. All mares were privately owned and utilized for the commercial production of thoroughbred races horses. All reproductive management of the mares was routine for the breeding farm and included negative uterine culture and cytology prior to breeding, daily monitoring when in estrus using rectal palpation and transrectal ultrasound examination associated with breeding. Ovulation inducing agents HCG (Chorulon, Intervet, De Soto, Kans.) or Deslorelin (SucroMate Equine, Thorn BioScience LLC, Louisville, Ky.) were administered to each mare prior to breeding. The mares were bred by natural service to one of 6 commercial thoroughbred stallions of known fertility. Mares were examined within 12-24 hours post breeding to monitor time of ovulation and determination of uterine fluid presence, quality and depth. All mares were bred once per estrus cycle by natural service. If uterine fluid was detected post-breeding, the mares were treated with oxytocin to facilitate uterine evacuation. In mares with the history of chronic endometritis or with excessive fluid present, uterine lavage and appropriate intrauterine antibiotics were utilized.

The mares were randomly assigned to be fed a commercial blended algal/flax seed omega-3 fatty acid supplement (Composition A) disclosed in the present invention, (FA-SUPPLEMENT mares; N=26), prior to breeding. This dose provided for a total of 14,400 mg of n-3 fatty acids daily of which 4,000 mg was DHA from a micro-algae source. The remainder of the n-3 fatty acid was provided from ground flax seed. The CONTROL mares (N=20) received no supplementation. All mares were maintained on pasture and supplemented with mixed grass/alfalfa hay and a custom pelleted ration formulated to provide the recommended mineral and nutritional requirements of nonlactating mares. Supplement feeding continued for approximately 60 days. The mares were bred as they became available to their respective stallions.

Intergroup comparisons were made using a nonparametric Kruskal-Wallis one-way analysis of variance or $\chi^2$ test at p<0.05. Data were analyzed using Statistix version 9.0 software (Student Edition of STATISTIX version 9.0, Analytical Software, Tallahassee, Fla.). Data are shown as means±standard deviation.

Example 2

FA Supplement Composition for Equine Reproductive Health

A general composition A for improving post-breeding inflammation, semen quality, and therefore, equine reproductive health, comprises: flaxseed meal, algal DHA, vitamin E, vitamin D3, sorbitol, ascorbic acid, alfalfa meal, sodium saccharin, propionic acid and artificial flavor. In one sample composition, the total omega-3 fatty acids is 7,200 mg, DHA is 2,000 mg, Vitamin D3 is 6000 IU, Vitamin E is 1000 IU, per 60 grams of total composition. In addition, such composition has 2% (w/w) protein, 32% (w/w) fat and 15% (w/w) fiber, by weight of the total composition. The omega-3-fatty acid is from fish-oil-free source, such as flaxseed. The DHA is also from an all-vegetarian, fish oil-free source.

For optimal benefits, mares and stallion are supplemented with this composition 30-60 days prior to breeding. In addition, the mares should be supplemented at least through 90 days of gestation and optionally through the entire gestation. Generally, feed 60 grams per 1100 lb of body weight daily. For example, for weanlings, 30 grams per day; for yearlings, 45 grams per day; for stallions, 12 grams per day; and for mares, 60-120 grams per day, such that, 120 grams per day through 90 days gestation and then maintain at a feeding rate of 60 gram per day through the rest of gestation.

Example 3

FA Supplement Increases the Per Cycle Pregnancy Rate

The overall per cycle pregnancy rate for FA-supplemented and Control mares was 1.49±0.40 cycles per pregnancy, which equates to a 76% per cycle pregnancy rate. The mean number of cycles per pregnancy was significantly lower for mares consuming FA-SUPPLEMENT compared to the CONTROL mares (1.19±0.40 vs. 1.59±0.81; P=0.03; FIG. 1).

Many factors influence the per cycle pregnancy rate of a stallion. Differences in individual inherent fertility and the quality of stallion management can have a significant influence. The age and reproductive status of a stallion's book of mares are a major determinant. It is generally assumed and has been demonstrated that maiden and foaling mares have the highest per cycle pregnancy rate of all classes of mares. It was reported that the per cycle pregnancy rates of individual stallions ranged from 49% to 79% which is consistent with the stallions in this study.

The breeding management in the present study would be considered optimal in several regards. All the mares and stallions were maintained on one farm under common husbandry and veterinary management. This situation would minimize much of the transport stress associated with the traditional model of mares traveling to stallion stations for breeding. Additionally, all mares were examined by a single experienced veterinarian who was able to schedule the mares for breeding at the optimal time. The average "book" or number of mares a Thoroughbred stallion breeds in a single breeding season is highly variable based on the stallion's popularity and market appeal. Based on statistics published by the Thoroughbred Jockey Club, the organization that provides oversight and registration for Thoroughbred horses, the average number of mares a Thoroughbred stallion bred in 2012 was 19. This ranges widely from a low of 6 to a high of 220 mares. The six stallions used in this study bred an average of 42 mares for the season. This number would permit optimum utilization of the stallion for maximum fertility.

The majority of the mares in this study were classified as "Barren" due to their failure to conceive in the previous breeding season or deliver a live foal in the current season due to early embryonic loss or abortion. Mares in this category are traditionally of lower fertility than "Maiden" or "Foaling" mares. Additionally, nine of the mares were bred to one stallion that was a known shedder of *Klebsiella pneumoniae* bacteria in his semen. *Klebsiella pneumoniae* is a gram negative bacterium that is a commonly cultured from the respiratory system, feces and reproductive tracts of horses. Some *Klebsiella* subtypes are frequently associated with endometritis in mares. Breeding to a stallion known to shed pathogenic bacteria in his semen also increased the incidence of post breeding inflammation and fluid retention. However, all of the mares bred to the "Shedder" stallion ultimately conceived. This would indicate the semen quality of the stallion was of acceptable potential fertility with regards to total number of progressively motile, morphologically normal spermatozoa required to achieve normal pregnancy rates when the breeding induced inflammatory response was modulated by postbreeding intrauterine therapy or ingestion of the N-3 fatty acid supplement.

Three of the mares bred to the stallion were in the group receiving the FA-supplement and six mares were in the Control group. The per cycle pregnancy rate was significantly lower (1.0 vs. 2.16; p<0.05) for the three mares that received the FA-supplement compared to the six mares that did not. Additionally, 3/6 (50%) of the Control mares had significant uterine fluid at 24 hours post breeding compared to 0/3 from the FA-supplemented mares (p<0.05). All mares bred to the "Shedder" stallion were routinely treated post breeding with an intrauterine infusion of antibiotics, Gentamycin sulfate (Gentamicin Sulfate, Vet-One, Columbus, Ohio, USA), at a dose of 2.0 grams diluted in 250 ml sterile saline. Three of the 6 Control mares that had significant uterine fluid present at 24 hours post breeding required additional therapy to resolve the post breeding inflammation. Uterine lavage with sterile saline was performed until the effluent was clear and then the antibiotic was infused into the uterus. Oxytocin (Vet-One, Columbus, Ohio, USA) (20 iu) was additionally administered 4-6 hours post lavage to facilitate uterine evacuation. However, the 3 FA-supplemented mares received no additional treatment.

Figure 2:
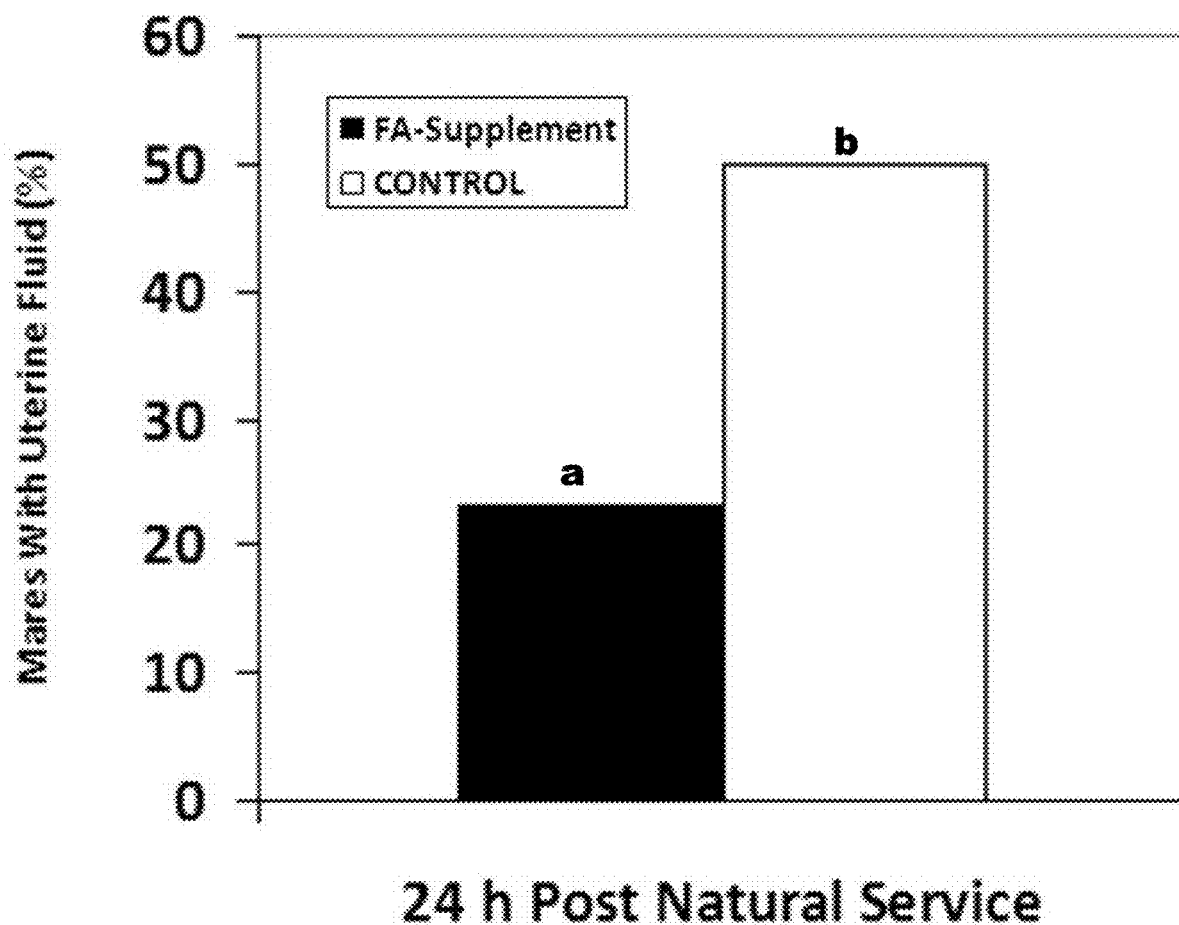
FIG. 2: Presence of uterine fluid in mares consuming FA-SUPPLEMENT or no supplementation (CONTROL) at 24 hours post natural service (7/26, 23% vs. 10/20, 50%). Different letters (a,b) indicate significant differences between treatments (P=0.05).

The overall presence of uterine fluid in FA-supplemented and Control mares was 58%. This is significantly greater than the overall rate of 15% that has been reported in other surveys of Thoroughbred mares. At 24 hours post natural service, significantly more CONTROL mares had uterine fluid present compared to FA-supplemented mares (10/20 vs. 7/26; P=0.05; FIG. 2). Additionally, 3/6 (50%) of the Control mares had significant uterine fluid at 24 hours post breeding compared to 0/3 from the FA-supplemented mares (p<0.05). The per cycle pregnancy rate was significantly lower (1.0 vs. 2.16; p<0.05) for the three mares that received the FA-supplement compared to the six mares that did not.

In conclusion, supplementation of Thoroughbred mares in a commercial breeding environment with a blended algal/flax n-3 fatty acid supplement resulted in significantly reduced post-breeding inflammation as evidenced by uterine fluid and improved per cycle pregnancy rates (FIG. 1 and FIG. 2).

Example 4

Effect of Docosahexaenoic Acid Supplementation on Early Postpartum Mare Reproductive Function Achieving conception on the first postpartum ovulation (foal heat) can be difficult in mares, yet this practice is often necessary to ensure annual foal production or to move up the birthdate of offspring to improve competitiveness in the sales or show ring. Supplementation of omega-3 (n-3) fatty acids (FA) has been shown to increase follicle size and oocyte viability and improve embryo quality and survival in many species of livestock. We hypothesized that docosahexaenoic acid (DHA) supplementation would hasten uterine involution, enhance folliculogenesis, and increase blood flow to reproductive tissues in the postpartum mare. Twenty stock breed mares (mean±SE, 624±10 kg) in their third trimester of gestation were randomly assigned to one of two dietary treatments: an n-3-rich fat supplement containing an algae source of DHA (n=10; Releira®, Arenus, St. Charles, Mo.) or a placebo fat supplement formulated to mimic the n-6:n-3 FA ratio (10:1) of the basal grain concentrate (n=10). Supplements were color-coded, thus blinding researchers to treatment and fed from 90 d prior to expected foaling through the first postpartum ovulation. On average, the DHA supplement provided 18.6, 10.5, and 2 g/d of fat, total n-3 FA, and DHA, respectively. The basal diet included grain concentrate, bahiagrass pasture and Coastal bermudagrass hay. Mares were observed during parturition to document labor-related events and examined daily thereafter by transrectal Doppler ultrasonography to measure uterine fluid clearance and involution, folliculogenesis, ovarian and uterine arterial blood flow, and blood perfusion to the dominant follicle. Data were analyzed using a one-way ANOVA or a mixed model ANOVA with repeated measures using time, treatment and time*treatment as fixed effects and horse within treatment as a random variable. Mares supplemented with DHA had a faster rate of involution of the non-gravid uterine horn (P=0.002) and increased blood flow in the ovarian artery ipsilateral to the dominant follicle (P=0.003) leading up to the first postpartum ovulation compared to placebo mares. Dietary treatment had no effect on gestation length (P=0.84), length of labor (P=0.82), latency to placental expulsion (P=0.67), placental weight (P=0.30), interval to first postpartum ovulation (P=0.29), rate of uterine fluid clearance (P=0.79), uterine body (P=0.43) or gravid horn involution (P=0.39), number or size of follicles (P>0.10), blood flow to the uterine arteries (P>0.10), or blood perfusion to the dominant follicle (P=0.74). Results indicate that low-level DHA supplementation does not alter gestation length or influence folliculogenesis, but hastens uterine involution of the non-gravid horn and increases ovarian blood flow in the postpartum mare. Future research should investigate the clinical impacts of DHA supplementation on uterine health and embryo quality/survival in broodmares.

Example 5

Maternal Supplementation of Docosahexaenoic Acid and its Effect on Fatty Acid Transfer to the Foal Docosahexaenoic acid (DHA) is an omega-3 (n-3) fatty acid (FA) important for neural function and is rapidly accumulated in the fetal brain during late gestation. Research in horses has shown that the most efficient means of increasing circulating DHA concentrations is via direct supplementation of DHA rather than n-3 FA precursors such as α-linolenic acid; however, limited data exists on DHA availability to the foal when supplemented to the mare. The objective of this study was to test the hypothesis that supplementing pregnant mares with DHA would increase DHA availability to foals, both in utero and during lactation, and facilitate passive transfer of immunity to the foal. Twenty (mean±SE, 624±10 kg) stock breed mares were randomly assigned to one of two dietary treatments: an n-3-rich fat supplement containing an algae source of DHA (n=10; Releira®, Arenus, St. Charles, Mo.) or a placebo fat supplement formulated to mimic the n-6:n-3 FA ratio (10:1) of the basal grain concentrate (n=10). Supplements were color-coded, thus blinding researchers to treatment and fed from 90 d prior to expected foaling through 74 d lactation. On average, the DHA supplement provided 18.6, 10.5, and 2 g/d of fat, total n-3 FA, and DHA, respectively. The basal diet included grain concentrate, bahiagrass pasture and Coastal bermudagrass hay. Umbilical cord blood collected at birth and venous blood samples collected from mares and foals before and during supplementation were analyzed for plasma and red blood cell (RBC) FA composition. Additionally, FA composition of mare colostrum and milk and immunoglobulin (Ig) concentrations in pre-suckle foal serum and colostrum were determined. Data were analyzed using a one-way ANOVA or a mixed model ANOVA with repeated measures using time, treatment and time*treatment as fixed effects and horse within treatment as a random variable. Mares supplemented with DHA had a greater proportion of DHA in plasma (P<0.0001), RBC (P=0.05), umbilical cord plasma (P=0.06), and total n-3 FA in plasma (P=0.01) and RBC (P=0.05) compared to placebo mares. Milk from DHA-supplemented mares had a higher concentration of DHA (P<0.0001), but similar total n-3 FA compared to placebo mares. Foals from DHA mares had a higher concentration of DHA (P<0.0001) and total n-3 FA (P=0.01) in plasma, but similar DHA and total n-3 FA in RBC compared to placebo foals. Mare colostrum and foal serum IgG, IgA, and IgM concentrations were unaffected by treatment. Results confirm that supplementing the mare with relatively low amounts of DHA can increase DHA transferred to her foal. Maternal DHA status has been linked to positive developmental outcomes in infants and may prove beneficial to the developing foal.

Example 6

Effect of Maternal Docosahexaenoic Acid Supplementation on Behavior and Cognitive Development in Nursing Foals Exposure to maternal docosahexaenoic acid (DHA) during gestation and lactation contributes toward improved mental development, childhood learning, and behavioral reactivity in humans. Although inclusion of fat in the diet of broodmares is common, the influence of maternal DHA intake on the behavior and cognitive development of their foals has not been examined. We hypothesized that supplementation of mares with DHA during late gestation and early lactation would positively influence innate behavior of foals at birth, early developmental behavior, and foal learning ability. Twenty (mean±SE, 624±10 kg) stock breed mares were randomly assigned to one of two dietary treatments: an omega-3-rich fat supplement containing an algae source of DHA (n=10; Releira®, Arenus, St. Charles, Mo.) or a placebo fat supplement formulated to mimic the omega-6 to omega-3 fatty acid (FA) ratio (10:1) of the basal grain concentrate (n=10). Supplements were color-coded, thus blinding researchers to treatment and fed from 90 d prior to expected foaling through 74 d postpartum. On average, the DHA supplement provided 18.6, 10.5, and 2 g/d of fat, total n-3 FA, and DHA, respectively. Foals were not directly supplemented, but did have access to their dams' feed. Latency to develop a suckle reflex, stand and nurse were recorded at parturition as measures of innate foal behavior. An ethogram was created to document play, social, and maintenance behaviors at 1 and 2 mo of age. Foal cognition was assessed at 2 mo of age as the rate of learning and scored performance on a series of operant conditioning tasks. Data were analyzed using one-way ANOVA or a zero inflated Poisson model. Foals born to DHA mares had a shorter latency to stand (P=0.09) and nurse (P=0.02) at parturition compared to foals born to placebo-supplemented mares. Foals exposed to DHA were more likely to engage in bouts of social affiliative (P=0.001), nursing (P=0.01), and lying down (P<0.0001) behaviors, while less likely to show alert behavior (P=0.005) compared to placebo foals. Colts were more likely (P=0.0002) to engage in bouts of play behavior compared to fillies; however, fillies exposed to DHA were more likely (P=0.09) to exhibit bouts of play compared to placebo fillies. Maternal dietary treatment did not affect foal scores (P=0.22) or the rate of learning (P=0.93) on progressive learning tasks, but colts were more likely (P=0.007) to receive perfect scores on tasks compared to fillies. Results indicate that exposure to maternal DHA supplementation positively impacts early innate and social behaviors.

Example 7

Influence of Dietary Algal N-3 Fatty Acids on Breeding Induced Inflammation and Endometrial Cytokine Expression in Mares Bred with Frozen Semen In the mare, acute inflammation that follows breeding is a normal physiologic response and necessary to facilitate clearance of contaminants, excessive sperm and seminal plasma from the uterus[1]. Omega-3 (n-3) fatty acids, particularly docosahexaenoic acid (DHA) has been shown to confer multiple health benefits in humans, lab animals and horses[2]. Recent studies in mares have presented data to support the role of cytokines in the process of postbreeding inflammation[3]. In multiple species, n-3 FAs inhibit the production of cytokines involved with acute and chronic inflammation[4]. The objectives of this study were to compare the uterine inflammatory response to frozen semen in resistant and susceptible mares before and after oral supplementation with a blended (algal DHA and flax seed) n-3 fatty acid product. The goal was to determine if significant differences existed in inflammatory response to frozen semen following supplementation as demonstrated by uterine fluid presence, cytologic parameters, endometrial cytokine expression and endometrial inflammatory cell infiltrate.

Fifteen mixed breed mares were used in the study. Ten mares (Mean age=5 years) were classified as Resistant based on age, history, endometrial biopsy scores of I-A or I-B, and ability to clear all evidence of mating induced endometritis at 24 hours post insemination when inseminated with $1.0 \times 10^9$ extended, cooled spermatozoa. Five mares (mean age=16 years) were classified as Susceptible based on endometrial biopsy scores of II-B and III and the presence of hyperechoic uterine fluid at 24 hours post insemination. Semen was collected and processed for freezing by routine methods to a final concentration of 200 million sperm/ml. To accentuate the potential inflammatory effect of dead sperm, the straws were subjected to 2 rounds of freezing and thawing and stored at −20° C. A dose of $1.0 \times 10^9$ total spermatozoa was used for each insemination. Estrus was induced and mares were monitored by transrectal ultrasonography. Uterine culture and cytology samples were obtained during estrus. Uterine biopsy samples were obtained from the base of both uterine horns. One uterine biopsy sample was placed in 10% formalin for histological analysis and the second biopsy sample was frozen in liquid nitrogen for m-RNA analysis of cytokines. Breeding management was routine with ovulation induction. Mares were examined every 12 hours post HCG treatment and were inseminated with $1 \times 10^9$ total spermatozoa when ovulation was imminent. Examinations continued every 6 hours post insemination to monitor time of ovulation and determination of uterine fluid presence, quality and depth. All mares were inseminated once per estrus cycle. At 24 hours post insemination uterine fluid samples were collected via low volume uterine lavage. The total volume of recovered uterine fluid, total number of cells and percent neutrophils were determined. Uterine biopsies were obtained from the base of each uterine horn and processed for histology and m-RNA analysis. A third set of endometrial biopsy samples were collected on Day 7 post-ovulation. Mares were administered a leuteolytic dose of cloprostenol to facilitate return to estrus. Following completion of the initial frozen semen challenge and sample collection, all mares were placed on a commercial, blended n-3 fatty acid supplement at a daily dose providing 14,400 mg of n-3 fatty acids of which 4,000 mg was DHA from a micro-algal source. The remainder of the n-3 fatty acid was provided from ground flax seed. Blood samples were collected on Days 0, 28 and 60 of treatment and the plasma was separated and stored frozen until analysis for fatty acid profiles. Supplement feeding was extended until the final sampling at Day 7 of the Day 60 challenge. On Day 60 all mares received leutolytic doses of cloprostenol to induce estrus and the frozen semen challenge, ultrasound monitoring and sampling of uterine fluid and endometrial biopsies repeated. Total RNA was isolated from 50 mg of endometrial tissue using the RNeasy total RNA kit. All RNA samples were treated with amplification grade DNAse I to remove any traces of genomic DNA. cDNA synthesis and relative quantification of IL-1 β, IL-6, and TNF-α mRNA expression were performed as previously described[3].

Figure 12:
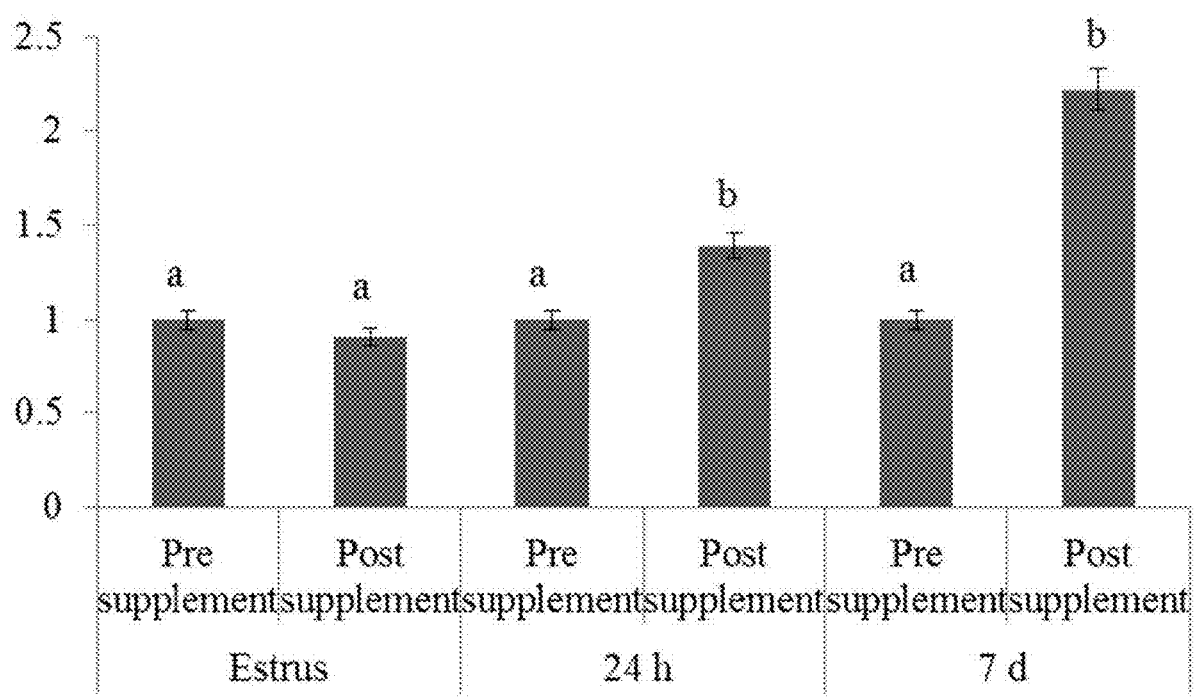
FIG. 12: Endometrial mRNA expression of IL-1 beta from mares (n=15) before and after 63+ Days of n-3 fatty acid supplementation. IL-1 beta was significantly up regulated at 24 h and 7 Days post insemination. Different superscripts between treatments within sampling time are different (P<0.05).

Plasma DHA levels (μg/ml) were significantly higher at D-28 (157.45±65.72) and D-60 (266.30±70.74) vs D-0 (0.00) p<0.001. There was no significant difference in uterine fluid (cm) at 6 hours post insemination (6.8±1.4 vs 5.4±1.3; p>0.05) between D-0 and D-63. At 12 hours (6.5±1.4 vs 2.3±1.2; p<0.05), 24 hrs (5.2±1.8 vs 1.3±1.3; p<0.05) and 7 Days post insemination (2.8±1.54 vs 0.0±0.0; p=0.05), significantly more fluid was present at D-0 vs D-63. A significant increase was noted in the mean number of neutrophils in endometrial tissue samples between the Pre and 24 hours post insemination sampling period at Day 0 and Day 63. Significantly more neutrophils (41.54±15.59 vs 13.33±5.88; p<0.01) were present on Day 7 before N-3 supplementation than after 63 Days of supplementation. At 7 Days post insemination, no significant differences were noted between D-0 and D-63 in mean number of neutrophils in endometrial tissue samples for the Resistant mares (n=10; 6.5±1.53 vs 5.33±1.88, p>0.05). For the Susceptible mares, significantly more neutrophils were noted for D-0 vs 63 (n=5, 45.7±4.53 vs 12.2±1.93, (p<0.05). Endometrial mRNA expression of IL-1 beta from mares (n=15) was significantly up regulated at 24 h and 7 Days post insemination following 63 Days of n-3 supplementation (P<0.05; FIG. 12). Endometrial mRNA expression of IL-6 from mares (n=15) was significantly up regulated at 24 h and 7 Days and expression of TNFα was significantly up regulated at 7 Days post insemination following 63 Days of n-3 supplementation.

The insemination challenge with $1 \times 10^9$ dead, frozen spermatozoa produced a significant inflammatory reaction in all mares, susceptible and resistant as evidenced by the presence of intrauterine fluid at 6 and 12 hours post insemination and significant neutrophil infiltration at 24 hours. This dose and processing, to kill the spermatozoa, was chosen to produce an exaggerated inflammatory response. Prolonged retention of fluid was observed in the 5 mares deemed to be susceptible to chronic endometritis. The inflammatory response as indicated by uterine fluid presence and neutrophil infiltration was significantly reduced at 12 and 24 hours in all classes of mares after 63+ days of n-3 FA supplementation. Of specific note was the very significant reduction in uterine fluid accumulation and neutrophil infiltration in the 5 mares deemed to be susceptible based on initial challenge. The decreased fluid presence at 12 hours in Susceptible mares following 63 Days of n-3 fatty acid supplementation could be due to the influence of n-3 fatty acids on reducing the inflammatory response to semen challenge. Alternatively, the reduced uterine fluid presence could be due to increased production of PGF2alpha by the endometrium thus increasing uterine contractility and evacuation. No differences in proinflammatory cytokine mRNA expression were noted between Susceptible and Resistant mares at the initial sampling time before the initial frozen semen challenge at Day 0. Up regulation of proinflammatory cytokine mRNA was observed in all mares following 63 Days of supplementation with the blended algal/flax seed n-3 supplement.

In conclusion, oral administration of an algae sourced N-3 fatty acid supplement to susceptible and resistant mares significantly reduced the post breeding inflammatory response to frozen semen.

References for Example 7:
[1] Troedsson, M H T, Alghmamdi A M, Mattisien J. Equine seminal plasma protects the fertility of spermatozoa in an inflamed uterine environment. *Theriogenology* 2002; 58:453-456.
[2] Hess T M, Rexford J, Hansen D K, Ahrens N S, Harris M, Engle T, Ross T, Allen K G. Effects of Ω-3 (n-3) fatty acid supplementation on insulin sensitivity in horses. *Journal of Equine Veterinary Science* September 2012, 1-11.
[3] Mette C, Dooleweerdt B C, Stine J et al. Evaluation of the systemic acute phase response and endometria gene expression of serum amyloid A and pro- and anti-inflammatory cytokines in mares with experimentally induced endometritis. Vet Immunol Immunopath 2010; 138:95-105.
[4] Wathes A C D., Abaasekara D R E, Aitken J R. Polyunsaturated fatty acids in male and female reproduction. *Biology of Reproduction* 2007; 77:190-201.

Example 8

Omega-3 Fatty Acids and Equine Airway Inflammations—Materials and Methods

Recruitment of Animals:

The database of the Veterinary Teaching Hospital of Purdue University was searched for horses diagnosed with chronic lower airway inflammatory condition in the past 5 years. Owners were contacted by mail and asked to enroll their horse in the study. Horses were considered for enrollment if they have history of chronic respiratory disease of at least 4-week duration and exhibit clinical signs of lower airway inflammation at the time of recruitment, evidenced by coughing, excessive mucous production in the trachea and/or increased respiratory effort at rest and exercise intolerance/poor performance. Baseline evaluation was conducted at Purdue University Veterinary Teaching Hospital (PUVTH) and horses underwent a complete physical exam and blood collection for complete blood count and animals with any signs of infectious respiratory condition or any concurrent disease at the time of recruitment were excluded. Horses that met the inclusion criteria were enrolled into the study.

Feed Supplement Administration and Housing:

Horses were randomly selected to receive omega-3 feed supplement (Composition B)(1× or 2× dose) or placebo as a top dressing on pelleted feed once daily for 8 weeks. During the study period horses were housed in their regular environment and fed a diet of complete pelleted feed based on individual energy requirements with no access to hay.

Vital Parameters and Body Weight:

Heart rate and respiration rate were determined with a stethoscope (Master Cardiology, Littmann, 3M Corp., MN, USA). Rectal temperature was measured with a digital thermometer (Vet One, Meridian Corp, China). Horses were weighed with a commercially available large animal scale.

Clinical Scoring System (CS):

Clinical scoring systems were used to assess respiratory compromise at the time of initial assessment and at the end of the supplementation period based on respiratory rate, respiratory effort, nasal discharge, and presence or absence of cough and abnormal lung sounds. A visual analog scale (VAS, score 0-100) was used by owners weekly at home to quantify performance, breathing difficulty and cough.

Dose Determination:

Eight horses (4 healthy and 4 RAO (Recurrent Airway Obstruction)) were divided into 2 groups. Horses underwent a thorough physical exam before enrollment into the study and venous blood samples were collected to determine plasma phospholipid profiles. Group 1 was started on the Omega-3 supplementation at the dose recommended by the manufacturer (1×). Group 2 was started on the Omega-3 supplementation at a double dose (2×). Horses were monitored daily for general attitude and appetite. Physical examination including clinical scoring was performed weekly. Blood was collected every 2 weeks to determine plasma phospholipid profiles. The dose of the supplement for each group was doubled every 2 weeks until a statistically significant reduction in omega-6:omega-3 ratio in serum and red blood cells was noted compared to baseline values, which was suggestive of adequate absorption and integration of the product. Once that dose was identified, horses were maintained on the same dose and blood samples were collected every 2 weeks to determine serum and red blood cell phospholipid profiles, until <10% change in omega-3:omega:6 ratio was identified compared to previous measurements, suggestive of a plateau effect. This dose was later used in efficacy study and referred to as 1×. Once plateau was reached, administration of the omega-3 supplementation was discontinued.

Efficacy Study:

The study was a double-blinded, randomized, placebo controlled trial. The included individual horses after a thorough examination were returned home and randomly assigned to receive one of three treatments (1× or 2× of omega-3 supplementation, or placebo) as a daily feed supplement for 8 weeks, while their attitude and appetite were monitored daily by the owners. They were maintained in the same environment as before enrollment but their diet was switched to a complete pelleted feed (e.g. Equine Senior, Purina Mills, St. Louis, Mo.). All medications were withheld during the study period. Owners were asked to repeat a VAS (Owner-assigned scores) for performance, breathing difficulty and cough once a week. At the end of the supplementation period (week 8), horses returned to PUVTH to repeat the work up. Both owners and clinicians were unaware of treatment assignments until after data collection was completed at the 2-month recheck.

Pulmonary Function Testing (PVF):

horses were restrained in stocks without sedation. Esophageal pressure and airflow measurements were computed to calculate maximum difference in transpulmonary pressure ($\Delta P_{Lmax}$), pulmonary resistance ($R_L$) and dynamic compliance ($C_{dyn}$). Then, horses were sedated with a combination of detomidine (0.02 mg/kg) and butorphanol (0.02 mg/kg) in preparation for BAL (Bronchoalveolar lavage).

Bronchoalveolar lavage was performed with a BAL tube advanced in the caudo-dorsal area of the left or right diaphragmatic lobes. Two hundred fifty mL of sterile 0.9% NaCl were infused and recovered by gentle aspiration. The BAL fluid was immediately placed on ice and processed within 20 minutes of collection. Cytological specimens were prepared by centrifugation and processed with Wright's stain. Isoprostane (8-Epi-PGF$_{2\alpha}$) concentration was quantified in BALF using a kit validated in the horse (Cayman Chemical Co, Ann Arbor, Mich.).

Blood Sample Collection:

Venipuncture was performed on the left or the right external jugular vein. Blood was collected with a 20G×1.5-inch needle into a 20 ml plastic syringe, transferred to EDTA containing tubes (BD Corp., NJ, USA). Complete blood count analysis was performed on a commercially available automated hematology analyzer.

As to the plasma fatty acid assay, each fatty acid (see Table 1A and Table 1B) was expressed as % of total fatty acids in plasma sample.

TABLE 1A

Examples of Saturated Fatty Acids:

| Common name | Chemical structure | C:D |
|---|---|---|
| Caprylic acid | $CH_3(CH_2)_6COOH$ | 8:0 |
| Capric acid | $CH_3(CH_2)_8COOH$ | 10:0 |
| Lauric acid | $CH_3(CH_2)_{10}COOH$ | 12:0 |
| Myristic acid | $CH_3(CH_2)_{12}COOH$ | 14:0 |
| Palmitic acid | $CH_3(CH_2)_{14}COOH$ | 16:0 |
| Stearic acid | $CH_3(CH_2)_{16}COOH$ | 18:0 |
| Arachidic acid | $CH_3(CH_2)_{18}COOH$ | 20:0 |
| Behenic acid | $CH_3(CH_2)_{20}COOH$ | 22:0 |
| Lignoceric acid | $CH_3(CH_2)_{22}COOH$ | 24:0 |
| Cerotic acid | $CH_3(CH_2)_{24}COOH$ | 26:0 |

TABLE 1B

Examples of Unsaturated Fatty Acids:

| Common name | Chemical name | Lipid name |
|---|---|---|
| Oleic acid | cis-9-octadecenoic acid | 18:1n9c |
| Vaccenic acid | cis-11-octadecenoic | 18:1n7 |
| Linoleic acid (LA) | all-cis-9,12-octadecadienoic acid | 18:2n6c |
| Rumelenic acid | 9E,11Z,15E-octadeca-9,11,15-trienoic acid | 18:3n3 |
| Arachidonic acid (AA) | all-cis-5,8,11,14-eicosatetraenoic acid | 20:4n6 |
| Eicosapentaenoic acid | all-cis-5,8,11,14,17-eicosapentaenoic acid | 20:5n3 |
| Docosadienoic acid | all-cis-13,16-docosadienoic acid | 22:2 |
| Docosahexaenoic acid (DHA, Cervonic acid) | all-cis-6,9,12,15,18,21-tetracosahexaenoic acid | 22:6n3 |

Statistical Analysis:

The effect of dose (1× vs. 2×) and disease status (healthy vs. RAO) were tested by analysis of covariance (ANCOVA) using post-treatment variable as outcome variable and pre-treatment variable as covariate. If significant effect was detected then, post-hoc analysis was conducted using Friedman analysis of variance (ANOVA) when comparing repeated measurements between week 0 and 8 or Mann-Whitney U test when comparing between groups at a given time point. In the efficacy study, the effect of dose (1× vs. 2×) and disease status (IAD vs. RAO) were tested using ANCOVA. Data were compared between baseline and 2 months following treatment with Wilcoxon matched pairs tests. Data were compared between treatment groups at each time point using Kruskal-Wallis ANOVA (3 treatment groups: Placebo, 1×, 2×) or Mann-Whitney U test (2 treatment groups: Placebo, composition supplementation [1× or 2×]). Owner-assigned scores (VAS) between week 0 and 8 were compared using Friedman ANOVA. Post-hoc paired comparisons of VAS scores between week 0 and subsequent weeks were performed using Wilcoxon matched pairs tests with Bonferroni adjusted p-value (0.05/7=0.0071; P<0.0071). All data were expressed as median[25%-75% quartiles]. P<0.05 was considered significant.

Example 9

FA Supplement Composition for Equine Respiratory Health

A general composition for improving airway inflammation diseases comprises: mushroom blend, DHA, mixed tocopherols, ascorbic acid, propionic acid, alfalfa meal, artificial flavor and sweeteners. In one sample composition of 30 gram in weight, there is 5,000 mg methylsulfonylmethane, 2,000 mg mushroom blend, 1,500 mg DHA and 1,000 mg ascorbic acid. The DHA is from an all-vegetarian, fish oil-free source.

For optimal benefits to maintain normal lung function and support respiratory and immune systems in horses, the horses having respiratory challenges due to seasonal allergies or overall immune deficiency are supplemented daily with this composition. Generally, an oral administration of 30 grams of the composition per 1100 lb of horse body weight daily provides support to equine's respiratory function and immune system.

Example 10

Dose Effect in Horses Supplemented Daily with Omega-3 FA

Figure 3A:
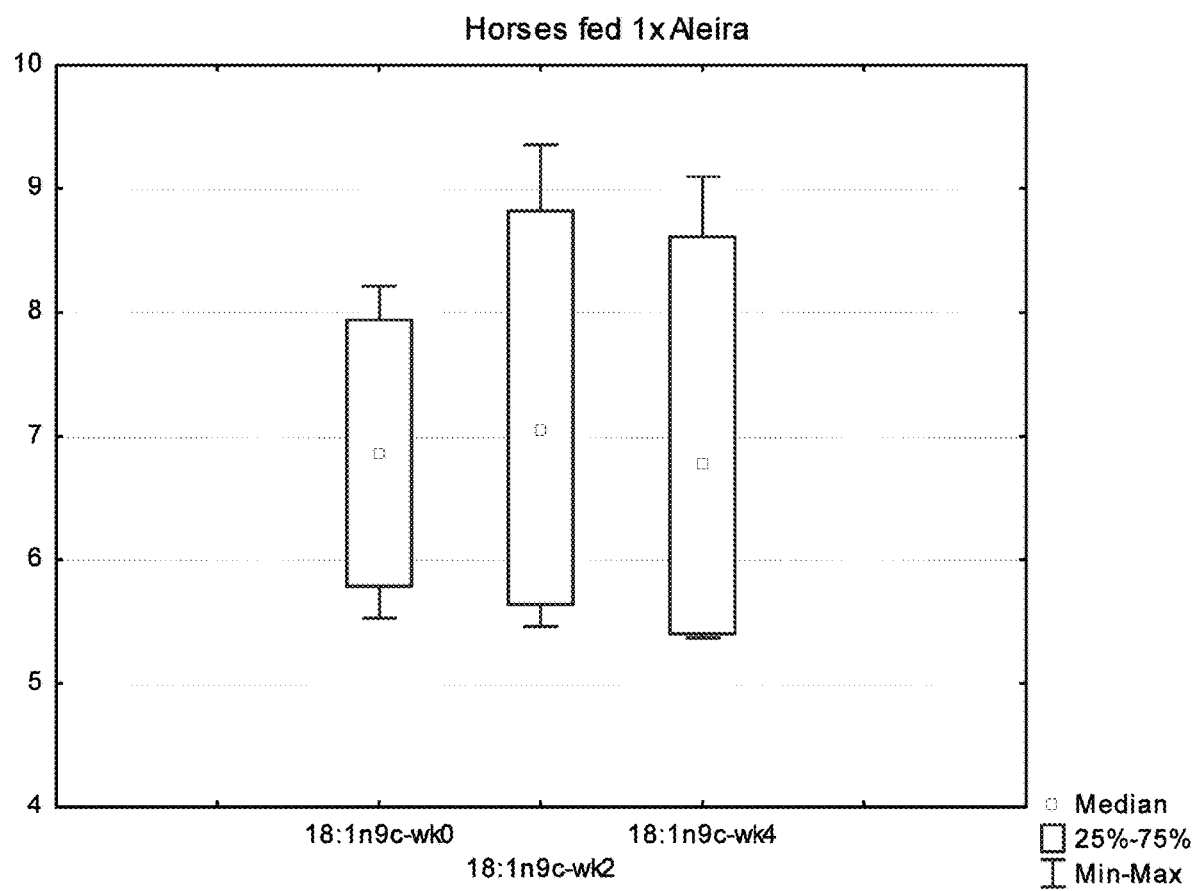
FIG. 3A and FIG. 3B: Plasma elaidic acid (18:1n9c; % of total fatty acids) in horses fed 1× (FIG. 3A) or 2× (FIG. 3B) Aleira during 4 weeks.
Figure 3B:
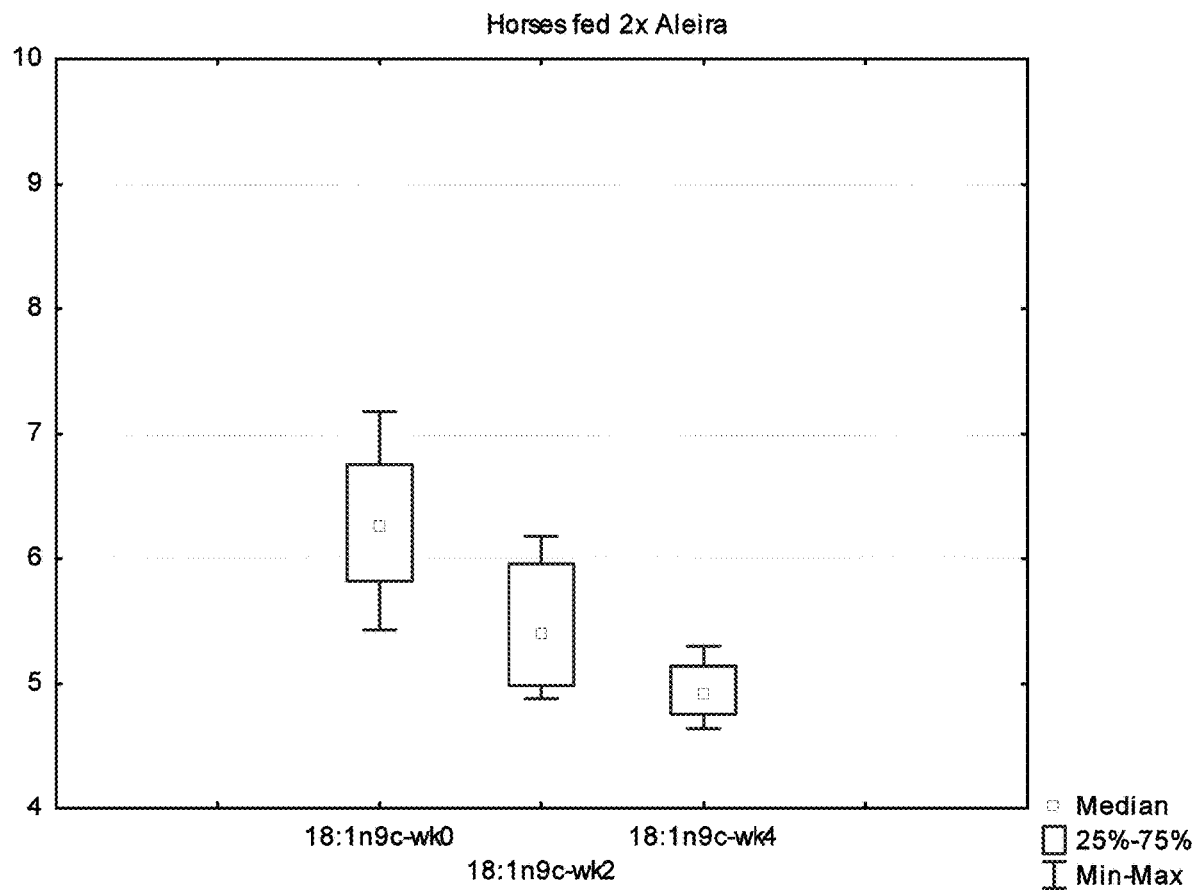
Figure 4:
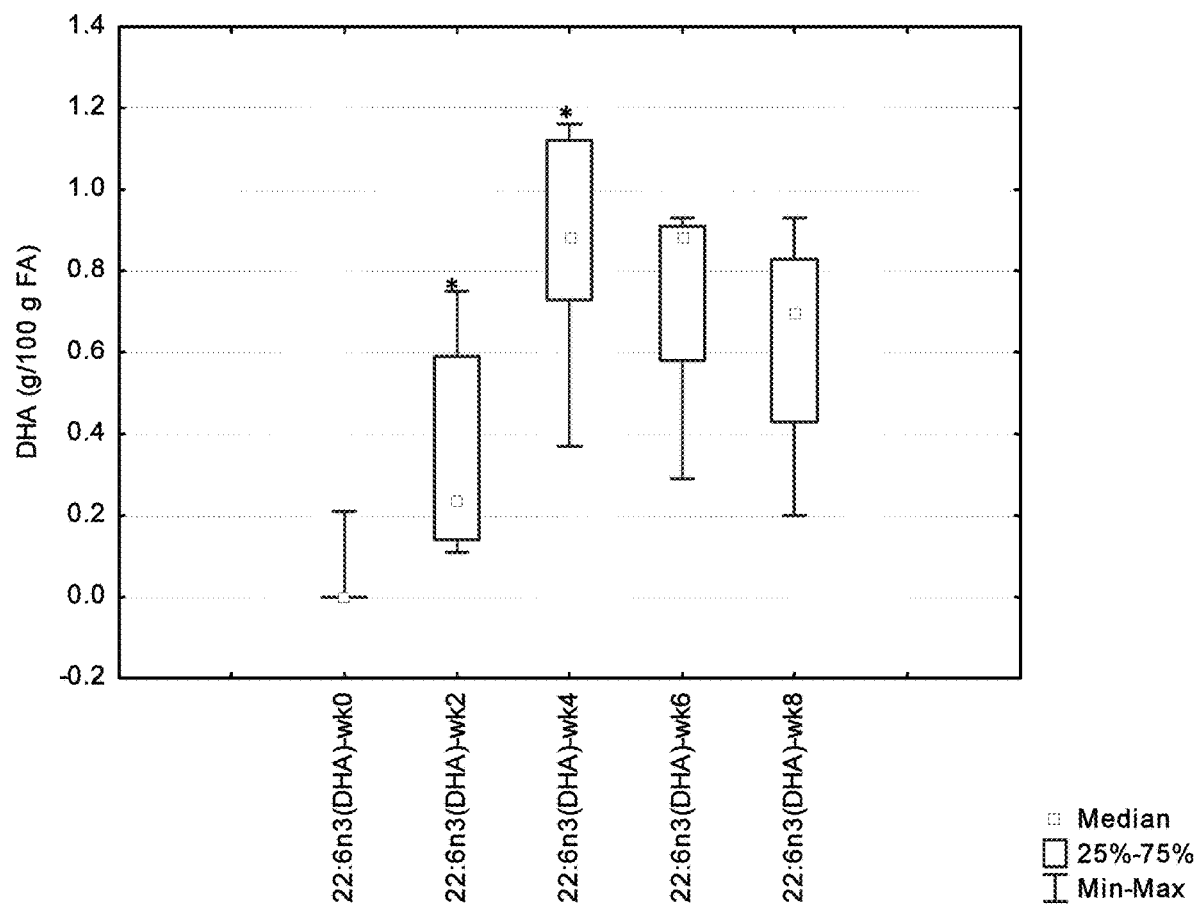
FIG. 4: Plasma DHA (% of total fatty acids) in horses fed daily Aleira during an 8-week period. * Significantly different from baseline (week 0; P<0.05).

There was no significant difference in plasma lipid proportions between healthy and RAO horses therefore, data from both groups were pooled. The only significant difference between doses (1× vs. 2×) was for elaidic acid (18:1n9c) where relative plasma levels decreased in horses receiving 2× dose during 4 weeks but not in those fed 1× dose (FIGS. 3A and B; P=0.018; also see Table 2-6). Subsequently, data from horses receiving 1× or 2× composition supplementation were pooled. The relative amount of docosahexaeonic acid (DHA; expressed as % of total fatty acids) increased significantly between week 0 and 4 of supplementation and then reached a plateau between week 4 and 8 (FIG. 4; P=0.012).

TABLE 2

Variables between placebo and treatment groups at Week 0

| | | v1 = 0 AND v2 = 1 | | | v1 = 0 AND v2 = 2 | | |
| --- | --- | --- | --- | --- | --- | --- | --- |
| Variable | Valid N | Median | Lower Quartile | Upper Quartile | Median | Lower Quartile | Upper Quartile |
| 14:0-wk 0 | 4 | 0.27000 | 0.21500 | 0.29000 | 0.21000 | 0.18000 | 0.34500 |
| 14:1-wk 0 | 4 | 0.07000 | 0.00000 | 0.17000 | 0.29000 | 0.06000 | 0.49000 |
| 15:0-wk 0 | 4 | 0.20500 | 0.17000 | 0.29000 | 0.20000 | 0.14000 | 0.32000 |
| 15:1-wk 0 | 4 | 0.05500 | 0.00000 | 0.11500 | 0.00000 | 0.00000 | 0.14000 |
| 16:0-wk 0 | 4 | 14.73000 | 14.06000 | 16.94500 | 15.42500 | 13.87500 | 18.97000 |
| 17:0-wk 0 | 4 | 0.63000 | 0.58000 | 0.76500 | 0.68500 | 0.44500 | 1.07000 |
| 18:0-wk 0 | 4 | 30.66500 | 27.99500 | 34.99500 | 34.84500 | 29.84000 | 42.42500 |
| 18:1n9c-wk 0 | 4 | 6.85500 | 5.78500 | 7.94000 | 6.27000 | 5.82000 | 6.75500 |
| 18:1n7-wk 0 | 4 | 1.23000 | 1.08000 | 1.37500 | 1.47000 | 1.37000 | 1.62000 |
| 18:2n6c-wk 0 | 4 | 40.15000 | 33.27000 | 41.93500 | 36.22000 | 19.40500 | 43.85000 |
| 18:3n3-wk 0 | 4 | 0.41500 | 0.24000 | 0.61500 | 0.13000 | 0.00000 | 0.36000 |
| 20:0-wk 0 | 4 | 0.31000 | 0.09000 | 0.46500 | 0.46000 | 0.15000 | 0.87500 |
| 20:4n6-wk 0 | 4 | 1.33500 | 0.76500 | 1.58000 | 0.63000 | 0.16500 | 1.05000 |
| 20:5n3-wk 0 | 4 | 0.00000 | 0.00000 | 0.00000 | 0.00000 | 0.00000 | 0.00000 |
| 22:2-wk 0 | 4 | 0.00000 | 0.00000 | 0.08000 | 0.00000 | 0.00000 | 0.00000 |
| 22:6n3-wk 0 | 4 | 0.00000 | 0.00000 | 0.00000 | 0.00000 | 0.00000 | 0.10500 |

TABLE 3

Variables between placebo and treatment groups at Week 2

| | | v1 = 0 AND v2 = 1 | | | v1 = 0 AND v2 = 2 | | |
| --- | --- | --- | --- | --- | --- | --- | --- |
| Variable | Valid N | Median | Lower Quartile | Upper Quartile | Median | Lower Quartile | Upper Quartile |
| 14:0-wk 2 | 4 | 0.30000 | 0.21000 | 0.30500 | 0.21500 | 0.19000 | 0.25000 |
| 14:1-wk 2 | 4 | 0.27000 | 0.18000 | 0.34000 | 0.25000 | 0.20500 | 0.30500 |
| 15:0-wk 2 | 4 | 0.28500 | 0.20500 | 0.41000 | 0.15500 | 0.06500 | 0.22000 |
| 15:1-wk 2 | 4 | 0.00000 | 0.00000 | 0.06500 | 0.00000 | 0.00000 | 0.00000 |
| 16:0-wk 2 | 4 | 15.02500 | 14.36500 | 16.42500 | 14.04000 | 12.52500 | 15.44500 |
| 17:0-wk 2 | 4 | 0.64000 | 0.57000 | 0.78500 | 0.64500 | 0.50000 | 0.79000 |
| 18:0-wk 2 | 4 | 30.01500 | 28.21500 | 31.42000 | 29.11000 | 27.95000 | 30.33000 |
| 18:1n9c-wk 2 | 4 | 7.05000 | 5.64000 | 8.82000 | 5.40500 | 4.98000 | 5.95500 |
| 18:1n7-wk 2 | 4 | 1.01000 | 0.88000 | 1.26000 | 1.16000 | 1.14500 | 1.22500 |
| 18:2n6c-wk 2 | 4 | 38.16000 | 35.17500 | 39.26500 | 43.26000 | 41.51500 | 43.68500 |
| 18:3n3-wk 2 | 4 | 0.47500 | 0.39000 | 0.53500 | 0.38500 | 0.25000 | 0.39500 |
| 20:0-wk 2 | 4 | 0.56000 | 0.35500 | 0.72000 | 0.64000 | 0.31500 | 0.84000 |
| 20:4n6-wk 2 | 4 | 1.20000 | 1.12500 | 1.30000 | 0.95000 | 0.92500 | 1.04500 |
| 20:5n3-wk 2 | 4 | 0.00000 | 0.00000 | 0.00000 | 0.00000 | 0.00000 | 0.00000 |
| 22:2-wk 2 | 4 | 0.00000 | 0.00000 | 0.00000 | 0.00000 | 0.00000 | 0.00000 |
| 22:6n3-wk 2 | 4 | 0.14000 | 0.12000 | 0.32500 | 0.49000 | 0.23500 | 0.71500 |

TABLE 4

Variables between placebo and treatment groups at Week 4

| | | v1 = 0 AND v2 = 1 | | | v1 = 0 AND v2 = 2 | | |
| --- | --- | --- | --- | --- | --- | --- | --- |
| Variable | Valid N | Median | Lower Quartile | Upper Quartile | Median | Lower Quartile | Upper Quartile |
| 14:00-wk 4 | 4 | 0.23000 | 0.17500 | 0.27500 | 0.14500 | 0.14000 | 0.17000 |
| 14:01-wk 4 | 4 | 0.10000 | 0.05000 | 0.11500 | 0.16500 | 0.07000 | 0.23500 |
| 15:00-wk 4 | 4 | 0.27500 | 0.22500 | 0.32000 | 0.28000 | 0.24500 | 0.32000 |
| 15:01-wk 4 | 4 | 0.00000 | 0.00000 | 0.06000 | 0.05500 | 0.00000 | 0.12000 |
| 16:0-wk 4 | 4 | 14.56000 | 14.46500 | 15.57000 | 13.71500 | 13.28500 | 14.46500 |
| 17:0-wk 4 | 4 | 0.58500 | 0.52500 | 0.67500 | 0.60500 | 0.53500 | 0.67500 |
| 18:0-wk 4 | 4 | 28.27000 | 26.94500 | 28.66500 | 29.58500 | 27.88500 | 31.84000 |
| 18:1n9c-wk 4 | 4 | 6.77500 | 5.40000 | 8.61000 | 4.92500 | 4.75500 | 5.14000 |
| 18:1n7-wk 4 | 4 | 0.94000 | 0.72500 | 1.23500 | 1.15500 | 1.05500 | 1.25500 |
| 18:2n6c-wk 4 | 4 | 37.93000 | 36.93000 | 39.03500 | 41.31500 | 39.34500 | 42.94500 |
| 18:3n3-wk 4 | 4 | 0.48000 | 0.43000 | 0.60500 | 0.40500 | 0.36500 | 0.42000 |
| 20:0-wk 4 | 4 | 0.48000 | 0.38500 | 0.53000 | 0.59500 | 0.42000 | 0.74000 |
| 20:4n6-wk 4 | 4 | 1.53000 | 1.22000 | 1.74500 | 1.10000 | 0.98000 | 1.33500 |
| 20:5n3-wk 4 | 4 | 0.11000 | 0.00000 | 0.28000 | 0.00000 | 0.00000 | 0.00000 |
| 22:2-wk 4 | 4 | 0.00000 | 0.00000 | 0.14500 | 0.00000 | 0.00000 | 0.00000 |
| 22:6n3-wk 4 | 4 | 0.88500 | 0.61500 | 1.03500 | 0.97500 | 0.73000 | 1.12000 |

TABLE 5

Variables between placebo and treatment groups at Week 6 v1 = 0 AND v2 = 1

| Variable | Valid N | Median | Lower Quartile | Upper Quartile |
|---|---|---|---|---|
| 14:0-wk 6 | 4 | 0.14000 | 0.11000 | 0.22500 |
| 14:1-wk 6 | 4 | 0.13000 | 0.08000 | 0.17500 |
| 15:0-wk 6 | 4 | 0.11500 | 0.08500 | 0.24500 |
| 15:1-wk 6 | 4 | 0.03000 | 0.00000 | 0.09000 |
| 16:0-wk 6 | 4 | 16.18500 | 15.61500 | 16.82500 |
| 17:0-wk 6 | 4 | 0.50000 | 0.46000 | 0.56000 |
| 18:0-wk 6 | 4 | 26.22500 | 26.03000 | 26.37000 |
| 18:1n9c-wk 6 | 4 | 7.79000 | 6.65500 | 8.87500 |
| 18:1n7-wk 6 | 4 | 0.70500 | 0.63000 | 0.82500 |
| 18:2n6c-wk 6 | 4 | 39.00000 | 37.06500 | 40.61000 |
| 18:3n3-wk 6 | 4 | 1.24500 | 0.87000 | 1.63500 |
| 20:0-wk 6 | 4 | 0.57000 | 0.49500 | 0.73000 |
| 20:4n6-wk 6 | 4 | 1.50500 | 1.19000 | 1.68500 |
| 20:5n3-wk 6 | 4 | 0.04000 | 0.00000 | 0.14000 |
| 22:2-wk 6 | 4 | 0.00000 | 0.00000 | 0.00000 |
| 22:6n3-wk 6 | 4 | 0.88000 | 0.58000 | 0.91000 |

TABLE 6

Variables between placebo and treatment groups at Week 8 v1 = 0 AND v2 = 1

| Variable | Valid N | Median | Lower Quartile | Upper Quartile |
|---|---|---|---|---|
| 14:00-wk 8 | 4 | 0.26000 | 0.20000 | 0.38500 |
| 14:01-wk 8 | 4 | 0.06000 | 0.00000 | 0.16000 |
| 15:00-wk 8 | 4 | 0.22500 | 0.15500 | 0.28000 |
| 15:01-wk 8 | 4 | 0.04500 | 0.00000 | 0.11000 |
| 16:0-wk 8 | 4 | 16.79000 | 16.37500 | 17.64000 |
| 17:0-wk 8 | 4 | 0.44500 | 0.40000 | 0.48000 |
| 18:0-wk 8 | 4 | 26.20500 | 24.98000 | 27.50000 |
| 18:1n9c-wk 8 | 4 | 7.75500 | 7.05000 | 9.73500 |
| 18:1n7-wk 8 | 4 | 0.54000 | 0.52500 | 0.71500 |
| 18:2n6c-wk 8 | 4 | 36.15000 | 35.75000 | 36.98000 |
| 18:3n3-wk 8 | 4 | 1.19500 | 0.85500 | 1.88000 |
| 20:0-wk 8 | 4 | 0.57500 | 0.53000 | 0.62500 |
| 20:4n6-wk 8 | 4 | 1.27000 | 0.84500 | 1.50500 |
| 20:5n3-wk 8 | 4 | 0.11000 | 0.04000 | 0.44000 |
| 22:2-wk 8 | 4 | 0.06000 | 0.00000 | 0.30500 |
| 22:6n3-wk 8 | 4 | 0.69500 | 0.43000 | 0.83000 |

Example 11

Treatment Effect in Horses Supplemented Daily with Omega-3 FA

A total of 35 horses were evaluated, 34 qualified (1 horse was affected by upper respiratory tract obstruction) and 32 completed the trial. The 32 horses completed the trial under pre-selected criteria which included a baseline evaluation and a recheck after 2 months on the feed supplement in addition to complete pelleted feed without hay. Twelve horses received placebo feed supplement, seven were fed the supplement at the recommended label dose (1×) and eight horses received twice the labeled dose (2×).

Figure 5:
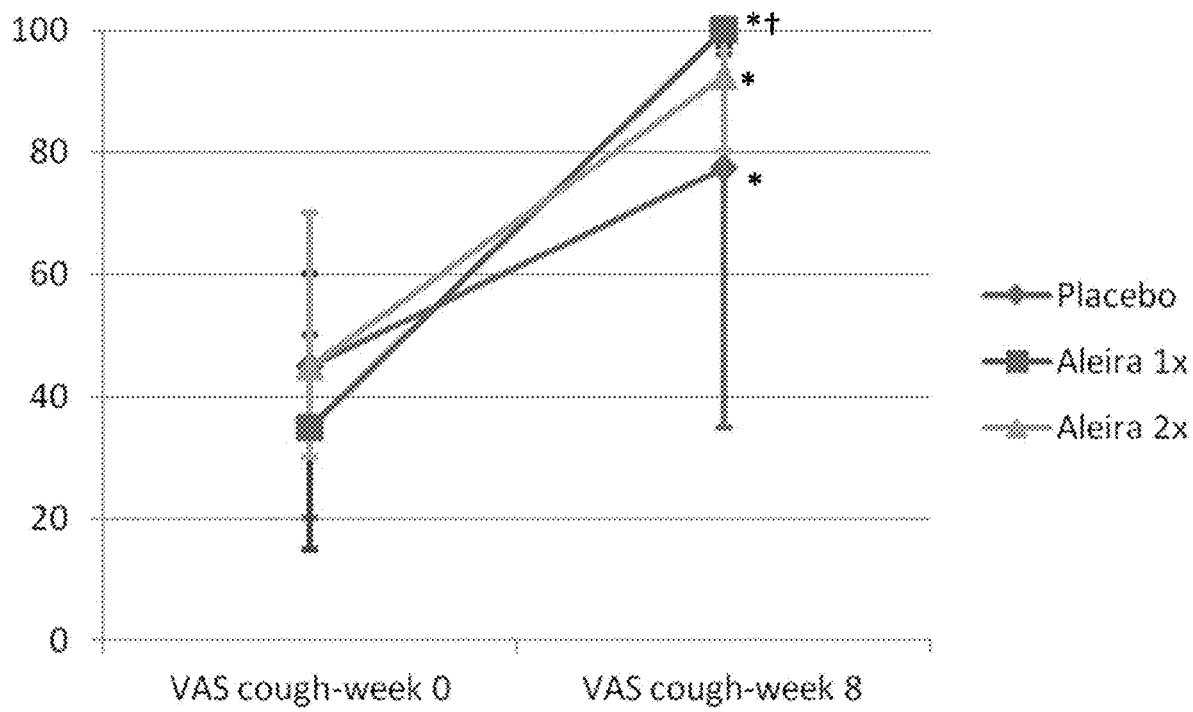
FIG. 5: Owner-assigned coughing score (VAS cough) before and 2 month after daily treatment with placebo or 1× or 2× dose of Aleira. * significantly different from baseline (week 0; P<0.05). † significantly different from placebo at week 8 (P=0.043).

All horses consumed the supplement (placebo and composition supplementation) and no adverse effects were reported by owners. No difference in treatment effect was detected between horses with RAO or IAD, therefore, data analysis was subsequently performed on data pooled among all horses with chronic respiratory disease. At baseline, none of the variables were different between placebo (v1=0) and treatment groups (v2=1 or v2=2; see also Table 7A and Table 7B). The only significant treatment effect related to the 2 composition supplementation doses (1×, 2×) was detected for VAS cough. Post-hoc analysis revealed that VAS cough improved significantly (i.e. increased) in all 3 treatment groups (placebo, 1×, 2×; see also Tables 2-6) however, horses treated with 1× dose of composition supplementation exhibited a significantly higher VAS cough score 2 month later than horses receiving placebo (FIG. 5, $P=0.043$).

Data from horses treated with 1× and 2× dose of composition for airway inflammation were pooled and compared to date from horses treated with placebo. Summary statistics for Long score, short score, VAS cough, VAS respiratory effort (VAS RE), VAS poor performance (VAS PP), dPmax, Cdyn, Macr %, Neut %, Eos %, Mast %, Lymph % at the beginning of the treatment (xxx1) and at 2-month (xxx2) are presented in Table 7A and Table 7B.

TABLE 7

Clinical scores, lung function variables and BAL fluid cytology before (1) and after 2 months (2) of supplementation with placebo (v2 = 0) or Supplement (v2 = 1)

Table 7A-Placebo group

Descriptive Statistics Include condition: v2 = 0

| Variable | Valid N | Mean | Median | Lower Quartile | Upper Quartile | Std. Dev. |
|---|---|---|---|---|---|---|
| Long score1 | 12 | 8.50000 | 9.00000 | 4.50000 | 11.00000 | 4.62208 |
| Short score1 | 12 | 4.66667 | 5.00000 | 4.00000 | 5.50000 | 1.61433 |
| VAS Cough1 | 12 | 39.16667 | 45.00000 | 20.00000 | 50.00000 | 22.34373 |
| VAS RE 1 | 12 | 43.33333 | 50.00000 | 30.00000 | 50.00000 | 21.88122 |
| VAS PP1 | 12 | 40.00000 | 45.00000 | 15.00000 | 60.00000 | 29.15476 |
| Long score2 | 12 | 5.58333 | 3.50000 | 3.00000 | 7.00000 | 5.19542 |
| Short score2 | 12 | 3.75000 | 3.00000 | 2.50000 | 5.00000 | 1.54479 |
| VAS Cough2 | 12 | 68.75000 | 77.50000 | 35.00000 | 95.00000 | 30.60934 |
| VAS RE 2 | 12 | 68.33333 | 75.00000 | 50.00000 | 90.00000 | 25.52479 |
| VAS PP2 | 12 | 65.41667 | 65.00000 | 40.00000 | 95.00000 | 30.70818 |
| dPmax1 | 8 | 11.59375 | 9.09500 | 7.47500 | 16.88000 | 5.78270 |
| Cdyn1 | 8 | 2.09875 | 1.93000 | 1.31500 | 2.80000 | 0.91487 |
| Rl1 | 8 | 0.85000 | 0.67000 | 0.46500 | 1.30000 | 0.47839 |

TABLE 7-continued

Clinical scores, lung function variables and BAL fluid cytology before (1) and after 2 months (2) of supplementation with placebo (v2 = 0) or Supplement (v2 = 1)

| | | | | | | |
|---|---|---|---|---|---|---|
| dPmax2 | 8 | 9.01323 | 6.61000 | 5.85500 | 9.26000 | 6.15110 |
| Cdyn2 | 6 | 2.47722 | 2.16665 | 1.20000 | 3.64000 | 1.54967 |
| RI2 | 6 | 0.63973 | 0.41000 | 0.23837 | 1.09000 | 0.52618 |
| Macr %1 | 11 | 38.72727 | 40.00000 | 27.00000 | 43.00000 | 15.79931 |
| Neut %1 | 11 | 19.63636 | 11.00000 | 7.00000 | 32.00000 | 16.23744 |
| Eos %1 | 11 | 0.90909 | 0.00000 | 0.00000 | 1.00000 | 2.07145 |
| Mast %1 | 11 | 2.81818 | 2.00000 | 1.00000 | 3.00000 | 2.44206 |
| Lymph %1 | 11 | 35.36364 | 34.00000 | 29.00000 | 48.00000 | 11.46536 |
| Macr %2 | 11 | 37.24545 | 41.00000 | 26.00000 | 48.00000 | 15.83549 |
| Neut %2 | 11 | 22.40909 | 17.00000 | 6.00000 | 29.00000 | 21.30824 |
| Eos %2 | 11 | 0.30000 | 0.00000 | 0.00000 | 0.30000 | 0.64031 |
| Mast %2 | 11 | 3.29091 | 3.00000 | 1.50000 | 5.00000 | 2.29367 |
| Lymph %2 | 11 | 36.24545 | 40.00000 | 26.00000 | 47.00000 | 14.58844 |

Table 7B-Supplemented group

Descriptive Statistics Include condition: v2 = 1

| Variable | Valid N | Mean | Median | Lower Quartile | Upper Quartile | Std. Dev. |
|---|---|---|---|---|---|---|
| Long score1 | 20 | 8.80000 | 8.5000 | 5.50000 | 12.0000 | 3.99473 |
| Short score1 | 20 | 4.60000 | 4.0000 | 4.00000 | 6.0000 | 1.69830 |
| VAS Cough1 | 18 | 46.66667 | 40.0000 | 20.00000 | 70.0000 | 28.90146 |
| VAS RE 1 | 18 | 52.77778 | 50.0000 | 20.00000 | 80.0000 | 31.95687 |
| VAS PP1 | 15 | 56.00000 | 50.0000 | 20.00000 | 90.0000 | 36.80062 |
| Long score2 | 20 | 3.40000 | 3.0000 | 2.00000 | 4.5000 | 2.08756 |
| Short score2 | 20 | 2.90000 | 2.5000 | 2.00000 | 4.0000 | 1.07115 |
| VAS Cough2 | 18 | 89.44444 | 100.0000 | 90.00000 | 100.0000 | 19.47010 |
| VAS RE 2 | 18 | 85.83333 | 92.5000 | 90.00000 | 100.0000 | 23.15231 |
| VAS PP2 | 15 | 80.00000 | 90.0000 | 75.00000 | 100.0000 | 30.87995 |
| dPmax1 | 18 | 19.49234 | 14.5200 | 7.54000 | 23.9100 | 15.92476 |
| Cdyn1 | 16 | 1.31995 | 1.3900 | 0.82000 | 1.5350 | 0.68189 |
| RI1 | 16 | 1.46318 | 1.3450 | 0.67000 | 1.5850 | 1.23481 |
| dPmax2 | 17 | 10.12597 | 7.5000 | 5.99000 | 13.2728 | 6.20609 |
| Cdyn2 | 15 | 2.87026 | 1.6500 | 1.27000 | 3.5000 | 2.76766 |
| RI2 | 15 | 0.75219 | 0.6100 | 0.28972 | 1.0900 | 0.48360 |
| Macr %1 | 19 | 29.68421 | 27.0000 | 21.00000 | 38.0000 | 14.39542 |
| Neut %1 | 19 | 31.44737 | 23.0000 | 13.00000 | 54.0000 | 25.05599 |
| Eos %1 | 19 | 0.31579 | 0.0000 | 0.00000 | 0.0000 | 0.67104 |
| Mast %1 | 19 | 2.68421 | 1.0000 | 0.50000 | 3.0000 | 3.10560 |
| Lymph %1 | 19 | 34.76316 | 38.0000 | 22.00000 | 47.5000 | 16.72354 |
| Macr %2 | 18 | 41.02778 | 40.3500 | 27.00000 | 48.0000 | 18.91672 |
| Neut %2 | 18 | 15.38333 | 8.5000 | 3.00000 | 20.0000 | 19.78928 |
| Eos %2 | 18 | 0.11667 | 0.0000 | 0.00000 | 0.0000 | 0.27279 |
| Mast %2 | 18 | 1.88333 | 1.0000 | 0.00000 | 2.0000 | 2.61472 |
| Lymph %2 | 18 | 40.12778 | 40.0000 | 28.00000 | 49.0000 | 19.28318 |

Figure 6:
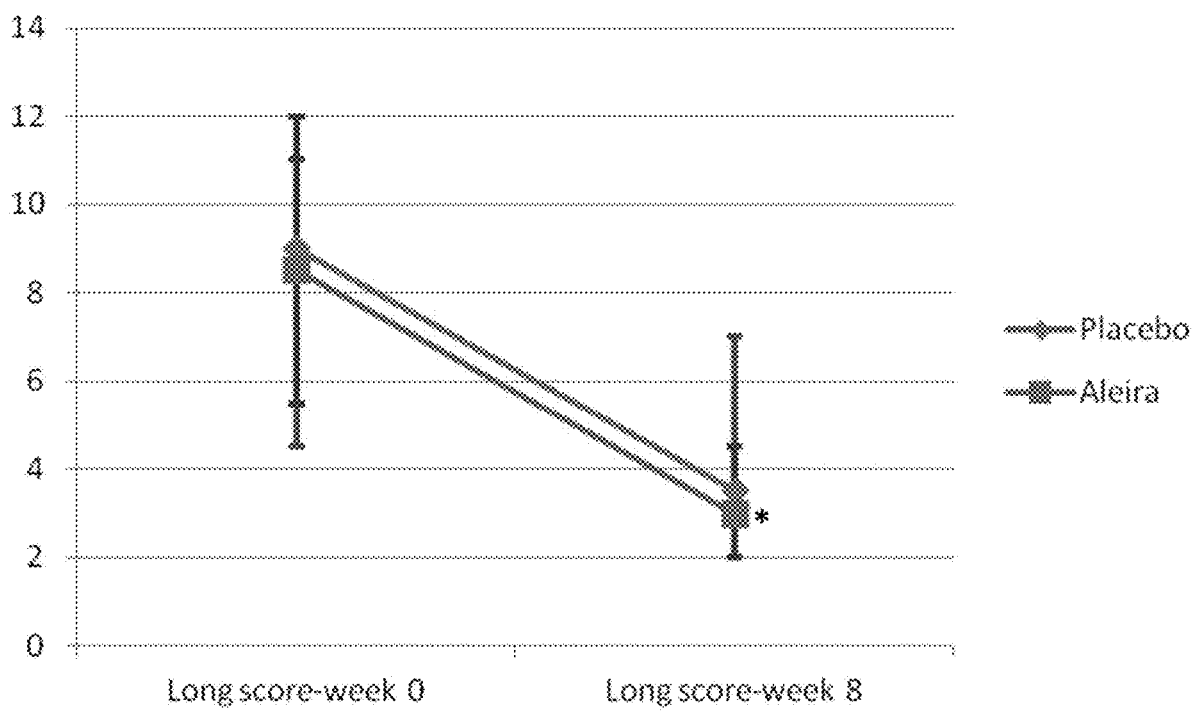
FIG. 6: Clinician-assigned long score (range: 0-21) in horses with chronic respiratory disease treated for 2 months with daily placebo or Aleira. * significantly different from baseline (week 0; P<0.05).

The effect of treatment with airway inflammation supplement on clinical signs was statistically significant as compared to placebo. Post-hoc analyses showed that clinician assigned clinical scores (long and short, Table 7A and Table 7B) in horses treated with composition supplementation (1× or 2×) exhibited a significant improvement (P<0.001) however, scores at 2-month were not different between placebo and composition supplementation treatments (FIG. 6)

Figure 7:
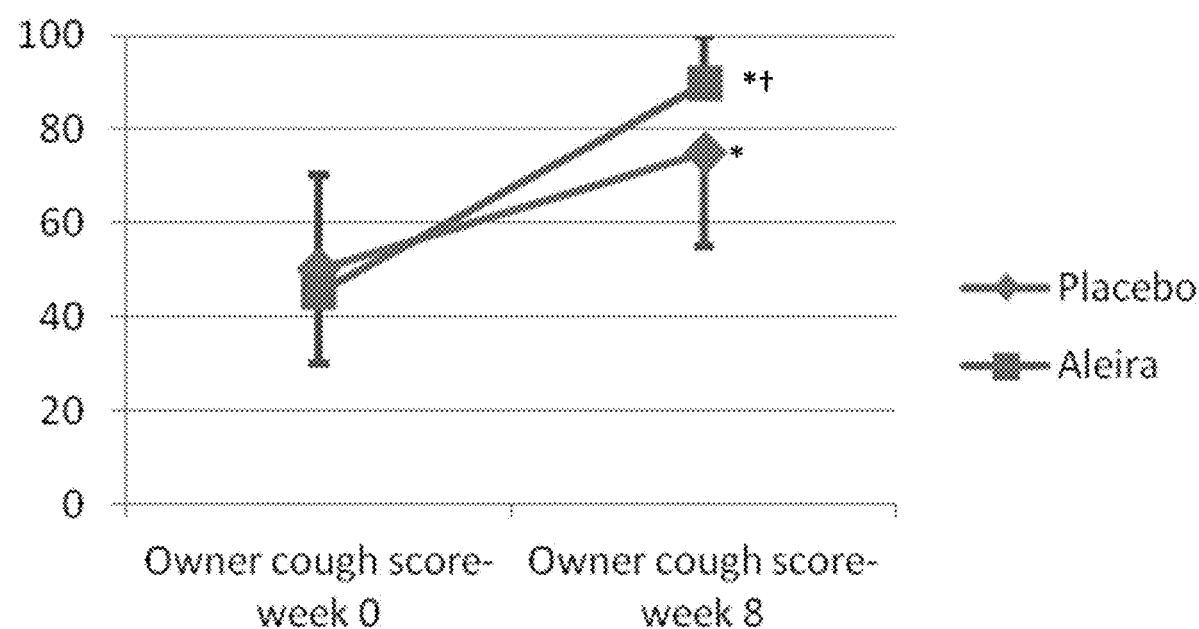
FIG. 7: Effect of feed supplementation on owner-assigned cough score of horses with chronic respiratory disease treated for 2 months. * significantly different from week 0 (P<0.05). † significantly different from placebo (P=0.031).

Owner-assigned clinical scores (VAS cough, respiratory effort, poor performance) improved significantly in placebo and composition supplementation treated horses, however, VAS cough and VAS respiratory effort scores 2 months after treatment were significantly higher in horses treated with composition supplementation compared to placebo (FIG. 7).

Figure 8A:
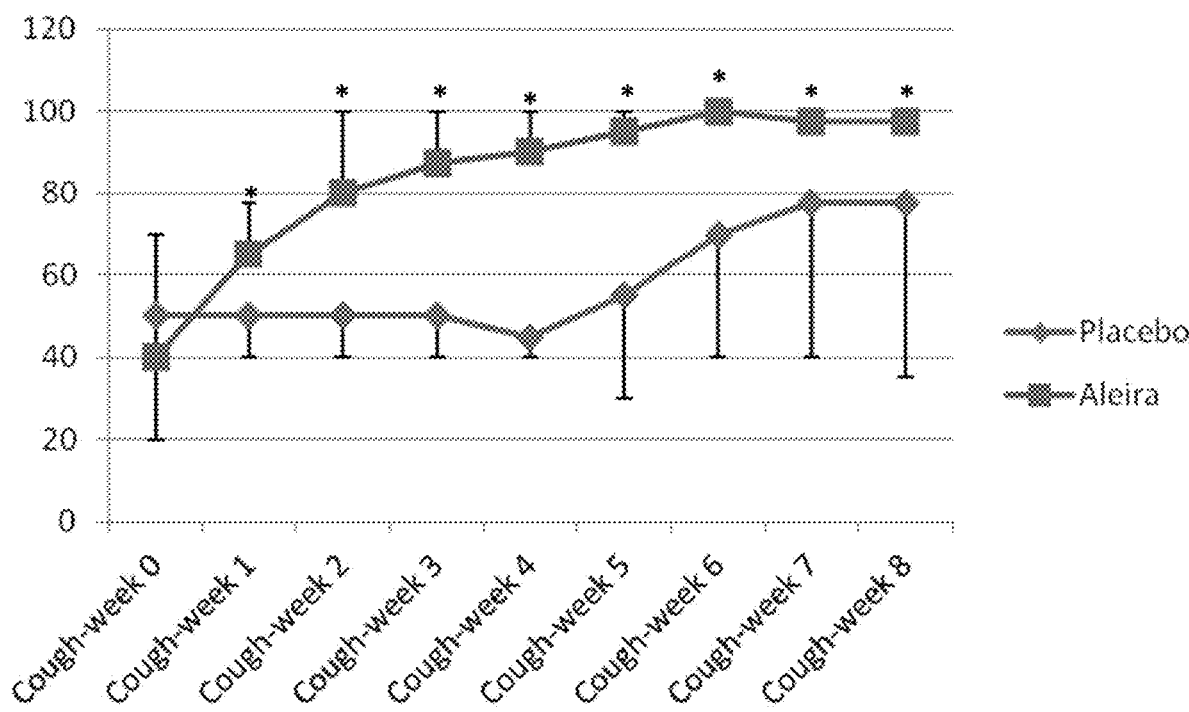
FIG. 8A and FIG. 8B: Weekly change in owner-assigned scores for cough (FIG. 8A) and respiratory effort (FIG. 8B) in horses fed a daily placebo or Aleira. * significantly different from week 0 (P<0.0071).
Figure 8B:
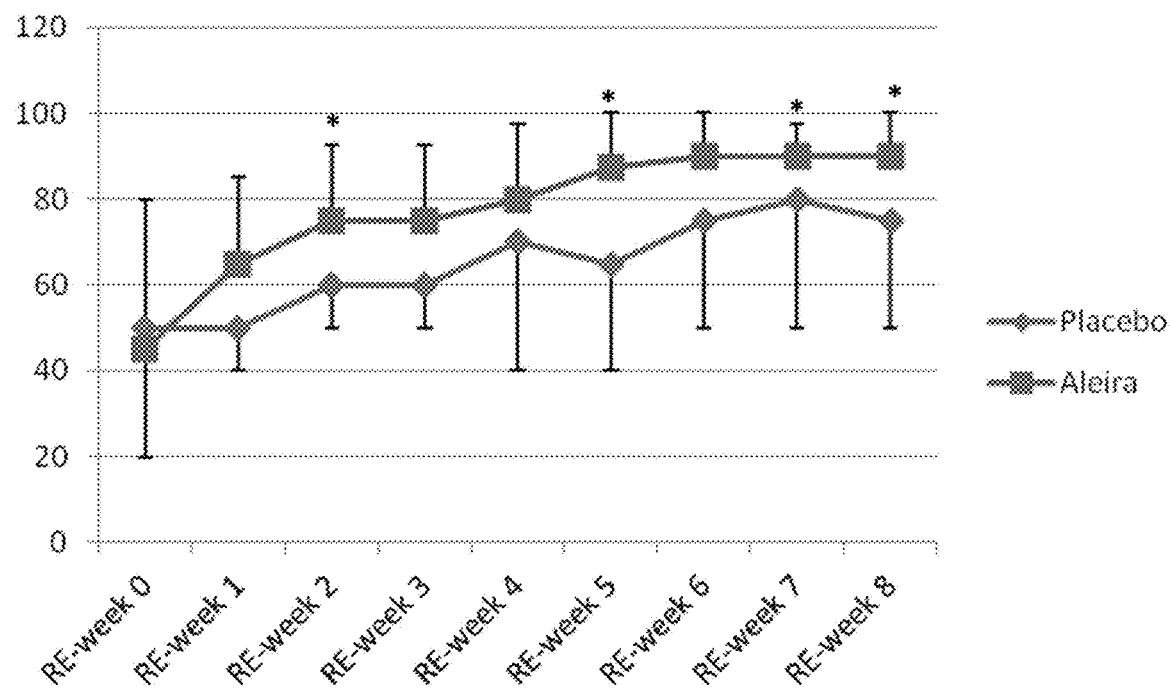

According to owners, the effect of composition supplementation and low dust diet on clinical signs were noticeable during the first 2 weeks of therapy and reached maximum benefit between weeks 2-5 for coughing (FIG. 8A), weeks 5-6 for respiratory effort (FIG. 8B) and weeks 3-5 for poor performance.

Figure 9:
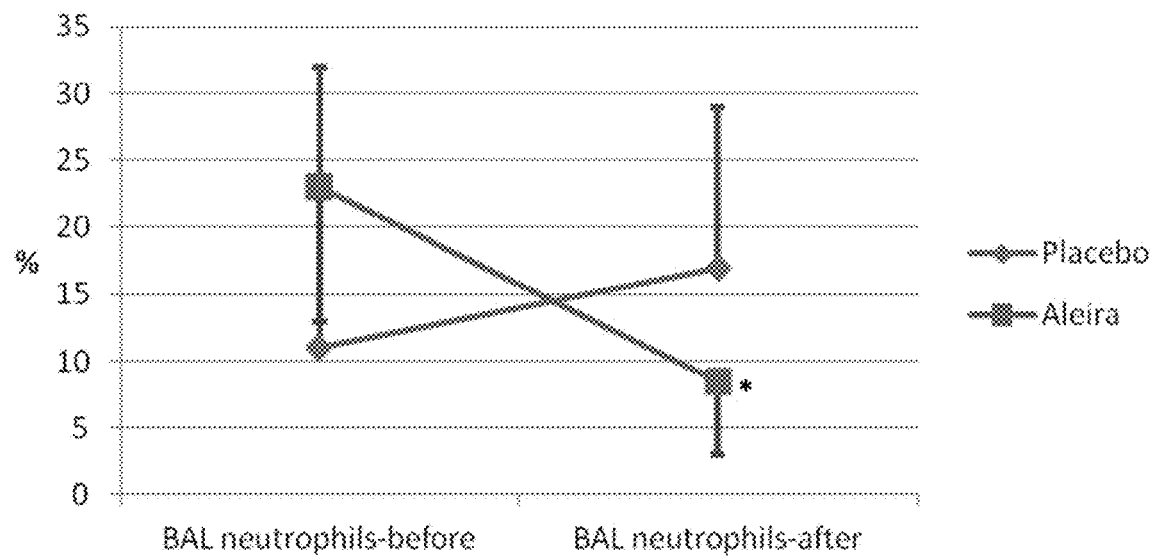
FIG. 9: Effect of feed supplementation on the proportion of inflammatory cells (neutrophils) in the bronchoalveolar lavage (BAL) fluid of horses with chronic respiratory disease treated for 2 months. * significantly different from week 0 (P=0.036).
Figure 10:
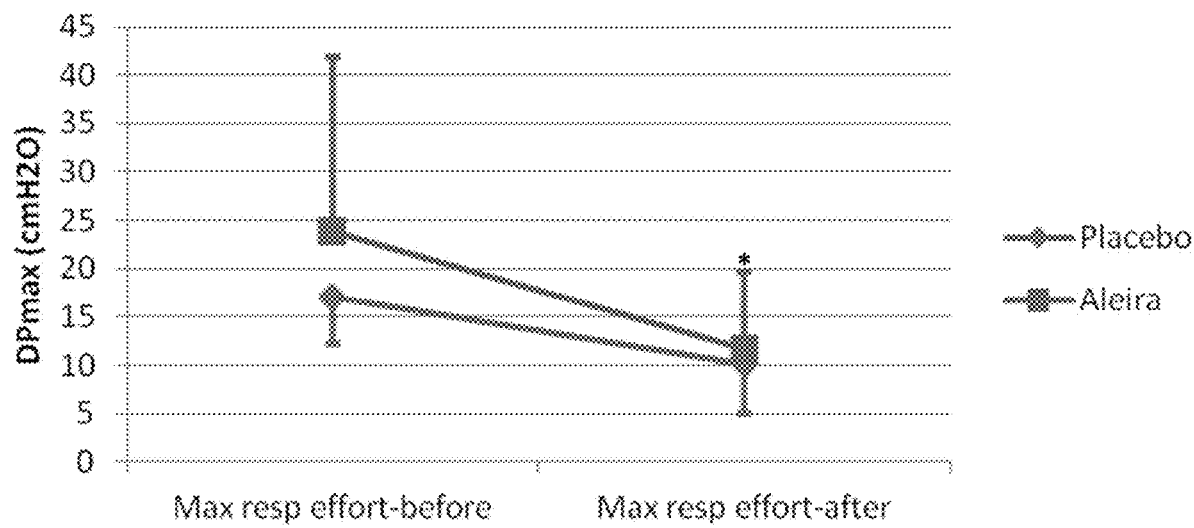
FIG. 10: Effect of feed supplementation on lung function (ΔPLmax) of horses with chronic respiratory disease treated for 2 months. * significantly different from week 0 (P=0.0065).

Composition supplementation for 2 months resulted in a significant decrease in the relative proportion of inflammatory cells (neutrophils) in the lung mucus whereas those cells didn't change significantly in horses fed the placebo (FIG. 9). Two months of feed supplementation improved lung function (decreased maximum respiratory effort [$\Delta P_{Lmax}$] and lung resistance [$R_L$]) in both placebo and composition supplementation treated horses, however, the effect was only significant in horses fed composition supplementation (FIG. 10).

Figure 11:
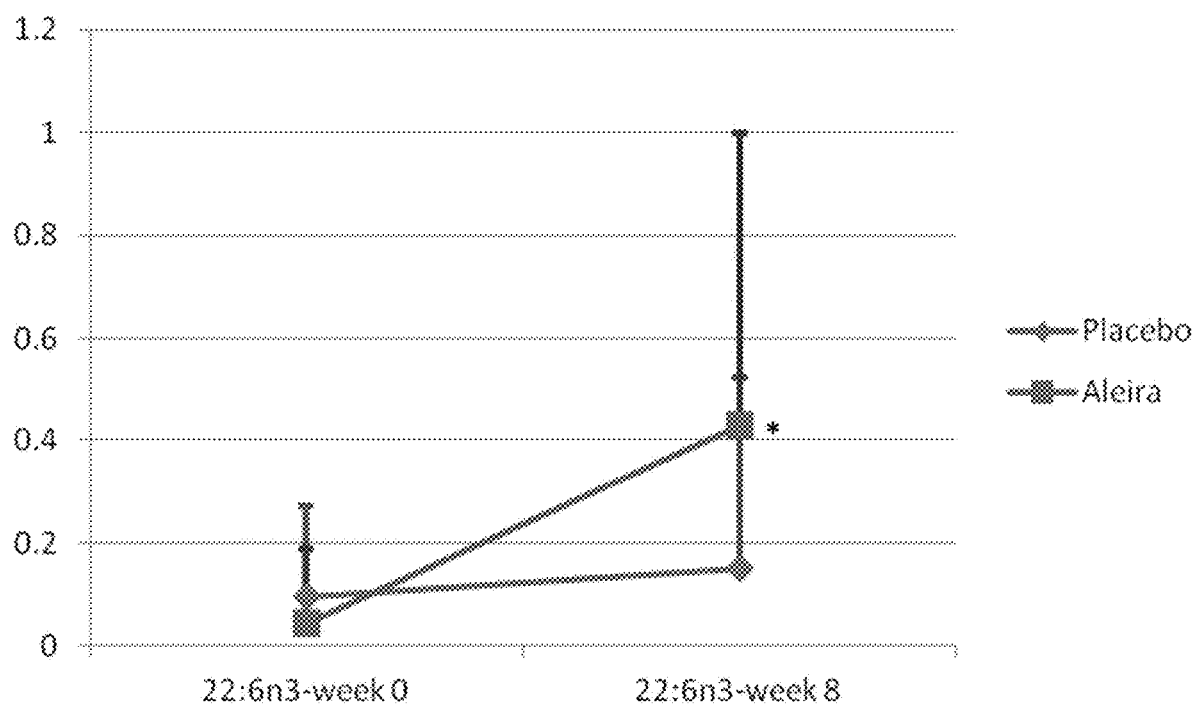
FIG. 11: DHA level expressed as % of total fatty acids in plasma sample of horses with chronic respiratory disease treated for 2 months. * significantly different from week 0 (P<0.001).

Relative amounts of selected PUFAs and isoprostane concentration at baseline (pre) and after 2 month of supplementation are shown in Table 8A (Placebo group) and Table 8B (Supplemented group). The only fatty acid that was significantly affected by composition supplementation treatment was DHA whereby 2 month of supplementation resulted in a 59% increase (P<0.001; FIG. 11). Isoprostane concentration in BAL was not significant affected by treatment.

TABLE 8

Relative amounts of selected PUFAs and isoprostane concentration
at baseline (pre) and after 2 month of supplementation (post)

Table 8A--Placebo group

Descriptive Statistics Include condition: v1 = 0

| Variable | Valid N | Mean | Median | Lower Quartile | Upper Quartile | Std. Dev. |
|---|---|---|---|---|---|---|
| 20:5n3-pre | 12 | 0.10847 | 0.04055 | 0.00000 | 0.24206 | 0.12385 |
| 22:6n3-pre (DHA) | 12 | 0.10027 | 0.09455 | 0.00000 | 0.17674 | 0.08798 |
| 20:5n3-post | 11 | 0.03372 | 0.00000 | 0.00000 | 0.00000 | 0.07508 |
| 22:6n3-post (DHA) | 11 | 0.20532 | 0.15027 | 0.00000 | 0.37134 | 0.27256 |
| Isoprostane-1 | 11 | 17.81889 | 13.40000 | 10.50000 | 20.70000 | 12.12416 |
| Isoprostane-2 | 11 | 17.17908 | 13.90000 | 6.94887 | 27.60000 | 11.82589 |

Table 8B-- Supplemented group

Descriptive Statistics Include condition: v2 = 1

| Variable | Valid N | Mean | Median | Lower Quartile | Upper Quartile | Std. Dev. |
|---|---|---|---|---|---|---|
| 20:5n3-pre | 20 | 0.08207 | 0.00000 | 0.000000 | 0.16200 | 0.10390 |
| 22:6n3-pre (DHA) | 20 | 0.09551 | 0.04480 | 0.000000 | 0.17103 | 0.11518 |
| 20:5n3-post | 17 | 0.13821 | 0.00000 | 0.000000 | 0.13775 | 0.33192 |
| 22:6n3-post (DHA) | 17 | 0.44997 | 0.42867 | 0.334087 | 0.57093 | 0.22248 |
| Isoprostane-1 | 19 | 16.28981 | 14.30000 | 9.000000 | 24.00000 | 9.24962 |
| Isoprostane-2 | 15 | 18.41731 | 13.40000 | 8.100000 | 28.00000 | 11.85649 |

Therefore, horses with chronic respiratory diseases such as RAO and IAD fed a low dust diet and supplemented with composition for airway inflammation experienced additional clinical benefits as compared to horses fed only a low dust diet. Improvement in clinical signs such as cough, respiratory efforts and performance were noticed within the first 2 weeks of therapy and full effect was observed between the second and sixth week. A single dose (1 scoop=30 g) of composition for airway inflammation appeared to result in similar benefit, if not more, than double dose (2 scoops=60 g). Besides the improvement in clinical signs associated with low dust management, supplementation of the composition for airway inflammation resulted in improvement in lung function and a decrease in the severity of airway neutrophilic inflammation however, oxidative stress as measured by BAL isoprostane was unchanged. These changes in clinical parameters were accompanied by a significant increase in the relative proportion of DHA in plasma of horses supplemented with composition for airway inflammation.

What is claimed is:

1. A method for reducing chronic respiratory disease in an equid, the method comprising administering 2-4 g per 110 lbs body weight for at least two weeks of a composition, wherein the composition comprises an all-vegetarian, fish oil-free source of DHA, methylsulfonylmethane (MSM), and between about 1000 and about 3000 mg per 30 g dose of a combination of *Pleurotus eryngii* mushrooms, *Cordyceps militaris* mushrooms, and *Ganoderma lucidum* mushrooms, wherein a portion of neutrophils in a lung mucus of the equid is reduced relative to the lung mucus of the equid prior to administration of the composition.

2. The method of claim 1, wherein the equid is further restricted to a hay free diet.

3. The method of claim 1, wherein the chronic respiratory disease is recurrent airway obstruction (RAO) or inflammatory airway disease (IAD).

4. The method of claim 1, wherein the composition further comprises mixed tocopherols and ascorbic acid.

5. The method of claim 1, wherein the composition comprises between 4500 mg and 5500 mg MSM per 30 g dose.

* * * * *